United States Patent [19]

Yoshimatsu et al.

[11] Patent Number: 5,185,431

[45] Date of Patent: Feb. 9, 1993

[54] RECOMBINANT NATURAL KILLER CELL ACTIVATOR

[75] Inventors: Kentaro Yoshimatsu; Yukio Ohya; Yasushi Shikata; Isao Tanaka; Yoshikazu Hasegawa; Toshio Seto, all of Ibaraki; Toshio Osawa, Tokyo, all of Japan

[73] Assignee: Eisai Co., Ltd., Tokyo, Japan

[21] Appl. No.: 392,841

[22] Filed: Aug. 11, 1989

[30] Foreign Application Priority Data

Aug. 31, 1988 [JP] Japan .............................. 63-217599

[51] Int. Cl.[5] ...................... C07K 13/00; A61K 37/02
[52] U.S. Cl. .................................. 530/351; 530/350; 530/395; 530/820; 435/69.5; 424/85.1; 930/120
[58] Field of Search ................ 530/350, 351, 395, 820; 435/69.5; 424/85.1; 514/2, 8; 930/120

[56] References Cited

FOREIGN PATENT DOCUMENTS 0083777 12/1982 European Pat. Off. .
0181524 10/1985 European Pat. Off. .
61-097224 10/1984 Japan .

OTHER PUBLICATIONS

McGrogan et al., J. Exp. Med., 168, 2295-2308 (1988).
Chemical Abstracts 103:52562z (1985).
Talmadge et al., Nature, vol. 284, pp. 622-624 (Apr. 17, 1980).
T. Maniatis et al., Molecular Cloning, Cold Spring Harbor Lab., pp. 320-321 (1982).
Okayama et al., Mol. and Cellular Biology, vol. 3, No. 2, pp. 280-289 (Feb. 1983).
Gluzman, Cell, vol. 23, pp. 175-182 (Jan. 1981).
Subramani et al., Mol. and Cellular Biology, vol. 1, No. 9, pp. 854-864 (Sep. 1981).
Southern et al., J. of Molecular and Applied Genetics, vol. 1, No. 4, pp. 327-341 (1982).
Kao et al., Proc. N.A.S., vol. 60, pp. 1275-1281 (1968).
Smith, Nucleotide Sequencing Techniques, vol. 58, pp. 560-581.
Galfre et al., Methods in Enzymology, vol. 73, pp. 3-47 (1981).
Sanger et al., Proc. Natl. Acad. Sci. USA, vol. 74, No. 12, pp. 5463-5467 (Dec. 1977).
Yokota et al., Proc. Natl. Acad. Sci. USA, vol. 82, pp. 68-72 (Jan. 1985).
Chirgwin et al., Biochemistry, vol. 18, No. 24, pp. 5294-5299 (1979).
Gubler et al., Gene, vol. 25, pp. 263-269 (1983).
Asada et al., Cellular Immunology, vol. 77, pp. 150-160 (1983).
Higuchi et al., Cellular Immunology, vol. 78, pp. 257-265 (1983).
Herberman et al., Immunological Rev., vol. 44, pp. 43-70 (1979).
Rygaard et al., Transplant. Rev., vol. 28, pp. 43-61 (1976).
Lathe, J. Mol. Biol., vol. 183, pp. 1 12 (1985).
Natural Killer, vol. 2, No. 2, pp. 70-75 (1984).
Shitara et al., The Journal of Immunology, vol. 134, No. 2, pp. 1039-1047 (Feb. 1985).
Kobayashi et al., The J. of Immunology, vol. 128, No. 6, pp. 2714-2718 (Jun. 1982).
Vose et al., The J. of Immunology, vol. 130, No. 2, pp. 768-772 (Feb. 1983).
Domzig et al., The J. of Immunology, vol. 130, No. 4, pp. 1970-1973 (Apr. 1988).
Science, vol. 183, pp. 534-537 (1973)—Stutman.
Kumagai et al., Japanese Handbook, vol. 42, pp. 859-868 (1984).
Shitura et al., J. Immunol 134(2) 1985, pp. 1039-1047, Prenderyast et al., J. Biol Chem. 263, 1988, pp. 12559-12563.

Primary Examiner—Garnette D. Draper
Attorney, Agent, or Firm—Birch, Stewart, Kolasch & Birch

[57] ABSTRACT

A recombinant natural killer cell activating factor is disclosed, preferably having a peptide of the following amino acid sequence in its molecule. The invention provides a cDNA coding for a recombinant natural killer cell activating factor, a expression plasmid involving the cDNA, a host transformed with the plasmid, an antitumor agent containing the recombinant natural killer cell activating factor and a pharmaceutical composition which comprises a pharmacologically effective amount of the antitumor agent and a pharmacologically acceptable carrier.

6 Claims, 13 Drawing Sheets

29-C-8 purification with monoclonal antibody column

Vydac C4.
0.1% TFA/acetonitrile
0-100% acetonitrile /30 min,
A280(0.32AUFS), 1.5ml/min

SDS-PAGE

1. Fr. 1
2. Fr. 2
3. Fr. 2 re-chromatography

Vydac C4  0.1% TFA/acetonitrile
0-60% acetonitrile /60min. A280(0.32AUFS)

FIG. 6

```
               10                                    20
LeuHisLeuArgSerGluThrSerThrPheGluThrProLeuGlyAlaLysThrLeuPro
├──KR-5──┤                                   ├─────────
├──────────────── KR-9 ────────────────┤
               30                                    40
GluAspGluGluThrProGluGlnGluMetGluGluThrProCysArgGluLeuGluGlu
─────────── KR-15,18 ───────────────┤

50                                    60
GluGluGluTrpGlySerGlySerGluAspAlaSerLysLysAspGlyAlaValGluSer
                                               ├─────────

70                                    80
IleSerValProAspMetValAspLysAsnLeuThrCysProGluGluGluAspThrVal
─KR-13──────────┤

90                                   100
LysValValGlyIleProGlyCysGlnThrCysArgTyrLeuLeuValArgSerLeuGln
      ├────── KR-8 ──────────┤                     ├──────
                                    ├── KR-10 ────────┤
              110                                   120
ThrPheSerGlnAlaTrpPheThrCysArgArgCysTyrArgGlyAsnLeuValSerIle
─ KR-19,20 ─────────────┤              ├──────────

130                                   140
HisAsnPheAsnIleAsnTyrArgIleGlnCysSerValSerAlaLeuAsnGlnGlyGln
─KR-16──────────┤
                                        ───────── KR-14 ──
              150                                   160
ValTrpIleGlyGlyArgIleThrGlySerGlyArgCysArgArgPheGlnTrpValAsp
    ├───── KR-1 ────┤            ├───── KR-12 ──
├─────────────┤                             ├──KR-11──
              170                                   180
GlySerArgTrpAsnPheAlaTyrTrpAlaAlaHisGlnProTrpSerArgGlyGlyHis
        ├──┤──── KR-21 ─────────┤
────────────┤                                   ├────

190                                   200
CysValAlaLeuCysThrArgGlyGlyTyrTrpArgArgAlaHisCysLeuArgArgLeu
         ├──KR-7────┤       ├── KR-2 ──┤─┤
─KR-6 ─────────────┤                     ├── KR-3 ──┤
              206
ProPheIleCysSerTyr
────KR-17─────┤
```

FIG. 9

```
         10        20        30        40        50
AGGAAGCAAAGAAGGACCTGGGCTTTGGGAAGATCTAAAGACCCAGGAAGGTCTCTGGGT 70        80        90       100       110
GGGATAAAGCCAAGATGAAACTCCCCTTACTTCTGGCTCTTCTATTTGGGGCAGTTTCT
            MetLysLeuProLeuLeuLeuAlaLeuLeuPheGlyAlaValSer 130       140       150       160       170
GCTCTTCATCTAAGGTCTGAGACTTCCACCTTTGAGACCCCTTTGGGTGCTAAGACGCTG
AlaLeuHisLeuArgSerGluThrSerThrPheGluThrProLeuGlyAlaLysThrLeu 190       200       210       220       230
CCTGAGGATGAGGAGACACCAGAGCAGGAGATGGAGGAGACCCCTTGCAGGGAGCTGGAG
ProGluAspGluGluThrProGluGlnGluMetGluGluThrProCysArgGluLeuGlu 250       260       270       280       290
GAAGAGGAGGAGTGGGGCTCTGGAAGTGAAGATGCCTCCAAGAAAGATGGGGCTGTTGAG
GluGluGluGluTrpGlySerGlySerGluAspAlaSerLysLysAspGlyAlaValGlu 310       320       330       340       350
TCTATCTCAGTGCCAGATATGGTGGACAAAAACCTTACGTGTCCTGAGGAAGAGGACACA
SerIleSerValProAspMetValAspLysAsnLeuThrCysProGluGluGluAspThr 370       380       390       400       410
GTAAAAGTGGTGGGCATCCCTGGGTGCCAGACCTGCCGCTACCTCCTGGTGAGAAGTCTT
ValLysValValGlyIleProGlyCysGlnThrCysArgTyrLeuLeuValArgSerLeu 430       440       450       460       470
CAGACGTTTAGTCAAGCTTGGTTTACTTGCCGGAGGTGCTACAGGGGCAACCTGGTTTCC
GlnThrPheSerGlnAlaTrpPheThrCysArgArgCysTyrArgGlyAsnLeuValSer 490       500       510       520       530
ATCCACAACTTCAATATTAATTATCGAATCCAGTGTTCTGTCAGCGCGCTCAACCAGGGT
IleHisAsnPheAsnIleAsnTyrArgIleGlnCysSerValSerAlaLeuAsnGlnGly 550       560       570       580       590
CAAGTCTGGATTGGAGGCAGGATCACAGGCTCGGGTCGCTGCAGACGCTTTCAGTGGGTT
GlnValTrpIleGlyGlyArgIleThrGlySerGlyArgCysArgArgPheGlnTrpVal 610       620       630       640       650
GACGGCAGCCGCTGGAACTTTGCGTACTGGGCTGCTCACCAGCCCTGGTCCCGCGGTGGT
AspGlySerArgTrpAsnPheAlaTyrTrpAlaAlaHisGlnProTrpSerArgGlyGly 670       680       690       700       710
CACTGCGTGGCCCTGTGTACCCGAGGAGGCTACTGGCGTCGAGCCCACTGCCTCAGAAGA
HisCysValAlaLeuCysThrArgGlyGlyTyrTrpArgArgAlaHisCysLeuArgArg 730       740       750       760       770
CTTCCTTTCATCTGTTCCTACTGAGCTGGTCCCAGCCAGCAGTTCAGAGCTGCCCTCTCC
LeuProPheIleCysSerTyr***

790       800       810       820       830
TGGGCAGCTGCCTCCCCTCCTCTGCTTGCCATCCCTCCCTCCACCTCCCTGCAATAAAAT 850       860
GGGTTTTACTGAAAAAAAAAAAAAAAA
```

```
         oligo #01
5'                                                                    3'
  GATAAAAAAAACAGTTGAATATTCCCTCAAAAATGAGATTTCCTTCAATTTTTACTGCA
  TTTTTTTTGTCAACTTATAAGGGAGTTTTTACTCTAAAGGAAGTTAAAAATG
3'                                                                    5'
```

FIG. B

RECOMBINANT NATURAL KILLER CELL ACTIVATOR

BACKGROUND OF THE INVENTION

This invention relates to a novel polypeptide which enhances the activity of natural killer cells (NK cells) in lysing human tumor cells; to a genetic engineering technique relating to the production thereof; and a drug containing said peptide as an active ingredient. Accordingly, the present invention is useful in the field of drugs.

BACKGROUND ART

It has been known that there are natural killer cells (NK cells) which show a destructive effect on specific cancer cells. Thus lymphokines affecting the activity of these NK cells have attracted attention. For example, it is reported that interleukin-2 and interferon enhance the activity of NK cells [Herberman, R. B., et al., Immunol. Rev., 44, 13 (1979); Vose, B. M., et al., J. Immunol., 130, 768 (1983); Domzig, W., et al., J. Immunol., 130, 1970 (1983)].

NK cells play various important roles as one of the non-specific host defense systems, for example, the first step of defense against cancer cells, suppression of the metastasis of cancer cells, resistance against viral infection and regulation of hematopoiesis in bone marrow [Kumagai, K. and Ito, K., Nippon Rinsho, Special Spring Issue, 42, 859 (1984)].

The following facts indicate that NK cells play important roles in the host defense against cancer. Namely, a nude mouse lacking T cells but having a high NK activity does not always suffer from spontaneous or chemically induced carcinogenesis at a high frequency [Rygaard, J. et al., Immunol. Rev., 28, 43 (1975); Stutman, D., et al., Science, 183, 534 (1974)]; and the metastasis of transplanted cancer cells is promoted in a beige mouse having T cells but a genetically low NK activity [Shimamura, K. and Tamaoki, K., Jikken Igaku, 2, 398 (1984); James, E., Talmadge, et al., Nature, 284, 622 (1980)] and a mouse having an artificially lowered NK activity [Shimamura, K. and Tamaoki, K., Jikken Igaku, 2, 398 (1984)].

Shitara et al. reported that an NK cell activity enhancing factor different from interleukin-2 is produced and liberated from mouse thymocytes [Shitara, K., Ichimura, O., Mitsuno, T. and Osawa, J., Immunol., 134, 1039 (1985)].

Some of the present inventors presumed the presence of a lymphokine capable of activating NK cells, established several cell lines of lymphokine producing human T cell hybridomas and demonstrated the presence of some lymphokines such as a macrophage migration inhibitory factor (MIF) and a macrophage activating factor (MAF) [Kobayashi, Y., Asada, M., Higuchi, M. and Osawa, T., J. Immunol., 128, 2714 (1982); Asada, M., Higuchi, M., Kobayashi, Y. and Osawa, T., Cell. Immunol , 77, 150 (1983); Higuchi, M., Asada, M., Kobayashi, Y. and Osawa, T., Cell. Immunol., 78, 257 (1983)].

In particular, they found that a human T cell hybridoma obtained from human T cells treated with keyhole limpet hemocyanin could produce a completely novel NK cell activating factor, which will be abbreviated to NKAF hereinbelow, different from any known lymphokine, as disclosed in Japanese Patent Laid-Open No. 97224/1986. In this invention, however, the obtained NKAF was a natural product per se and the amino acid sequence thereof as a peptide was not clearly specified;

In order to apply an NKAF as a drug on an industrial scale, it is necessary to clarify the amino acid sequence thereof as a peptide and to mass-produce it as a recombinant DNA product obtained through a genetic engineering technique.

Thus the present inventors have attempted to isolate and identify the NKAF which enhances the activity of NK cells so as to obtain its gene.

Accordingly, it is a first object of the present invention to purify the natural NKAF disclosed in the Japanese Patent Laid-Open No. 97224/1986 and to specify the partial amino acid sequence thereof It is a second object of the present invention to select a specific cDNA clone from a cDNA library prepared from the mRNA of the human T cell hybridoma based on the abovementioned sequence to thereby finally obtain a recombinant NKAF product.

As the first step for achieving the above-mentioned objects, the present inventors purified the natural NKAF by immuno-affinity column chromatography and specified the partial amino acid sequence thereof.

Next, they selected a desired cDNA clone from a cDNA library prepared from the mRNA of the human T cell hybridoma (C-108) based on the amino acid sequence (KR-21) specified above. Subsequently the amino acid sequence of the NKAF was specified from the base sequence of the cDNA clone pNK8308 thus obtained. Further the recombinant NKAF was expressed and its activity was confirmed.

Based on these findings, they have conducted further examination, thus completing the present invention.

Now the present invention will be described in detail.

SUMMARY OF THE INVENTION

The invention provides a recombinant natural killer cell activating factor is disclosed, preferably having a peptide of the following amino acid sequence in its molecule. The invention provides a cDNA coding for a recombinant natural killer cell activating factor, an expression plasmid including the cDNA, a host transformed with the expression plasmid, an antitumor agent containing the recombinant natural killer cell activating factor and a pharmaceutical composition which comprises a pharmacologically effective amount of the antitumor agent and a pharmacologically acceptable carrier.

```
                    10
LeuHisLeuArgSerGluThrSerThrPheGluThrProLeu

20
GlyAlaLysThrLeuProGluAspGluGluThrProGluGln 30                      40
GluMetGluGluThrProCysArgGluLeuGluGluGluGlu

50
GluTrpGlySerGlySerGluAspAlaSerLysLysAspGly 60                      70
AlaValGluSerIleSerValProAspMetValAspLysAsn

80
LeuThrCysProGluGluGluAspThrValLysValValGly

90
IleProGlyCysGlnThrCysArgTyrLeuLeuValArgSer
```

-continued

```
                100                           110
       LeuGlnThrPheSerGlnAlaTrpPheThrCysArgArgCys

120
       TyrArgGlyAsnLeuValSerIleHisAsnPheAsnIleAsn 130                           140
       TyrArgIleGlnCysSerValSerAlaLeuAsnGlnGlyGln

150
       ValTrpIleGlyGlyArgIleThrGlySerGlyArgCysArg

160
       ArgPheGlnTrpValAspGlySerArgTrpAsnPheAlaTyr 170                           180
       TrpAlaAlaHisGlnProTrpSerArgGlyGlyHisCysVal

190
       AlaLeuCysThrArgGlyGlyTyrTrpArgArgAlaHisCys 200              206
            LeuArgArgLeuProPheIleCysSerTyr
```

The final target product of the present invention may be produced through genetic engineering techniques.

Therefore a cDNA coding for the recombinant NKAF of the present invention and an expression plasmid containing said cDNA and obtained by linking in such a manner as to enable the regulation and expression in a selected host, both of which are intermediates required in the production of the final target product of the present invention, constitute the present invention together to thereby contribute to the solution of the same problem.

Furthermore, a host transformed with said expression plasmid also constitute the present invention like the abovementioned cDNA and expression plasmid As the host, *Escherichia coli,* yeasts and animal cells such as BHK cells and CHO cells may be employed.

An example of an *E. coli* strain carrying the cDNA is one discriminated as XL1-Blue/pNK 8308 B which will be described in Example 1. The strain has been deposited with Fermentation Research Institute as FERM P-10161, now transferred to the international deposit, FERM BP-2468.

The recombinant NKAF of the present invention, i.e., the final target product has an antitumor activity, as will be shown in Examples hereinafter.

Similar to the natural NKAF which is available as an active ingredient of a drug composition and applied to medical uses, therefore, the recombinant NKAF of the present invention may be used as an active ingredient of a drug composition to thereby apply its activity to therapeutic purposes.

In this case, said drug composition may be usually formulated into an intravenous injection.

The injection may be prepared in a conventional manner employed in the art in the formulation of a trace amount of a physiologically active substance into an injection.

For example, the recombinant NKAF of the present invention may be formulated into an aqueous solution either alone or together with appropriate filler(s) or solubilizing agent(s), filtered under sterile conditions, packed lyophilized and combined with an aqueous solution for dissolution. Thus an injection which is to be dissolved at use may be prepared.

Now the production and determination of the natural NKAF will be described. 1. Production of purified natural NKAF:

In order to produce the recombinant NKAF, the purification of the natural NKAF and the analysis of its structure are conducted in the following manner.

Natural NKAF may be purified from a serum-free culture supernatant of a clone C-108 line of natural NKAF-producing human T cell hybridoma KC-8-1-10 (cf. Japanese Patent Laid-Open No. 97224/1986) through various methods including ion exchange chromatography, gel filtration chromatography, affinity chromatography and high performance liquid chromatography.

The determination of the N-terminal amino acid sequence of the purified NKAF thus obtained and the amino acid sequence of a purified NKAF fragment peptide obtained by enzymatically digesting the same with trypsin enable the cloning of the cDNA.

The effect of the NKAF in enhancing the NK activity may be determined by utilizing the activity of plastic-nonadherent human peripheral blood lymphocytes (plastic-nonadherent PBLs) in killing human cancer cell line K-562 cells (NK activity) as the guiance. Namely, a sample is subjected to double-serial dilution with an RPMI-1640 medium containing 10% of fetal calf serum (10% FCS-RPMI-1640). 50-$\mu$l portions of the diluted samples were introduced into a 96-well microplate. Next $1\times10^5/50$ $\mu$l of the plastic-nonadherent PBLs were added thereto and incubated therein at 37° C. for 16 hours. Then $1\times10^4/100$ $\mu$l of a $^{51}$Cr-labeled K-562 cell suspension was added thereto and incubated therein at 37° C. for additional four hours.

Separately, 100 $\mu$l of the 10% FCS-RPMI-1640 medium was incubated for 16 hours and then 100 $\mu$l of a $^{51}$Cr-labeled K-562 cell suspension was added thereto, followed by incubating for additional four hours as a control. The released $^{51}$Cr in 100 $\mu$l of the incubation is determined.

$$NK\ activity\ (\%) = (b-a)/(c-a) \times 100$$

In the above equation, b represents liberated $^{51}$Cr (cpm) of the sample; a represents liberated $^{51}$Cr (cpm) of the control; and c represents total $^{51}$Cr (cpm) in 100 $\mu$l of the $^{51}$Cr-labeled K-562 cell suspension ($10^5$/ml). The determination is to be conducted triplicate and the mean value is calculated.

The NKAF activity corresponding to 50% of the maximum enhancing effect under these conditions may be defined as 1 U.

An example of the production of the natural NKAF is as follows.

(1) Purification of Natural NKAF

A human T cell hybridoma KC8-1-10 C-108 line was grown in a 10% FCS-RPMI-1640 medium in a 10-1 glass jar until the cell density reached 1 to $2\times10^6$ cells/ml.

After the completion of the incubation, the cells were collected by centrifugation and washed with RDF medium. The washed cells were suspended in the RDF medium in such a manner as to give a density of $1\times10^6$ cells/ml. The obtained suspension was continuously incubated in a glass jar at 37° C. for 14 to 20 days.

The supernatant was continuously replaced with a fresh one at a rate of 10 l/day and the target NKAF was purified from the NKAF-containing supernatant by the following method.

200 l of the serum-free culture supernatant was filtered through a glass fiber filter paper GF/F available from Whatman Inc. to remove cell debris. The filtrate was eluted through a column packed with sepabeads SP-900 available from Mitsubishi Chemical Ltd., a gel volume of 2 l. at a flow rate of 25 l/hr to remove hydrophobic low molecular weight substances such as phenol red. The eluates were pooled and the electric conductivity thereof was adjusted to that of a 10 mM Tris-HCl buffer (pH 8) containing 0.2M of NaCl. Then it was treated with a DEAE-Sepharose column (mfd. by Pharmacia; gel vol.: 2 l) equilibrated with the 10 mM Tris-HCl buffer (pH 8) containing 0.2M of NaCl at a flow rate of 12 l/hr. This column was washed with the same buffer and then eluted with a 10 mM Tris-HCl buffer (pH 8) containing 0.6M of NaCl.

4 l of the eluted fraction showing the NKAF activity was concentrated approximately 1000-fold on an ultrafiltration membrane (YM-5, mfd. by Amicon). The concentrated fraction was then treated with a Sephadex G 75 gel filtration column [mfd. by Pharmacia; 50 (i.d.)×900 mm] equilibrated with a 0.1M aqueous solution of $NH_4HCO_3$ at a flow rate of 100 ml/hr to thereby remove high molecular weight substances such as nucleic acids. Active fractions were pooled and combined. The combined active fractions (approximately 900 ml) were concentrated approximately 20-fold on a YM-5 membrane and then lyophilized.

The lyophilized matter thus obtained was then dissolved in 5 ml of a mixture of 0.1M $CH_3COONa$ buffer (pH 5) with 0.1M $Na_2SO_4$ buffer (pH 5) (1:1).

The solution thus obtained was adsorbed by a Phenyl-5PW-RP column for fractionation [mfd. by Tosoh, 21.5 ϕ×150 mm]. Then it was eluted by using eluent A [0.1M $CH_3COONa$ buffer(pH 5)/0.1M $Na_2SO_4$ buffer (5.0)=1/1] and eluent B [eluent A/$CH_3CN$=1/1].

The elution was conducted by linearly increasing the proportion of the eluent B from 0 to 100% within three hours to thereby elute the NKAF.

Thus the main fraction was eluted during the retention time of 100 to 110 minutes and some portion thereof was eluted during 110 to 140 minutes under the above conditions.

It was confirmed that these active fraction could react with monoclonal antibodies, which will be described hereinafter, by EIA.

Thus the main active fractions eluted during the retention time of 100 to 110 minutes were collected, lyophilized and were obtained the partially purified natural NKAF.

BRIEF DESCRIPTION OF THE DRAWINGS

FIGS. 5 and 6 show each the amino acid sequence of a peptide chain.

FIG. 9 shows the base sequence of the cDNA of pNK 8308 and the amino acid sequence of NKAF deduced therefrom.

(2) PREPARATION OF MONOCLONAL ANTIBODY FOR NATURAL NKAF AND ITS COLUMN

The partially purified natural NKAF obtained by the above process (1), which was used as an immunizing antigen, was mixed with Freund's complete adjuvant to thereby give an emulsion. 0.2 ml/animal of this emulsion was intraperitoneally administered to mice thrice to thereby immunize these animals.

Next, the partially purified natural NKAF was administered to mice through the tail veins and the spleen of each animal was taken out three days thereafter. The spleen cells thus obtained was fused with mouse myeloma cells X63-Ag 8,6,5,3 (Flow Lab.) by using 45% polyethylene glycol 3350 (mfd. by Sigma).

Subsequently the fused cells were grown in a conventional manner [Galfré, G. and Milstein, C. et al., Methods in Enzymology, 73, 3 (1981)].

Then two types of hybridoma cells 19-E-7 and 29-C-8 producing an antibody absorbing the NKAF activity were selected.

The obtained hybridoma cells were transplanted into the abdominal cavities of mice, to which 0.5 ml portions pristane of (Aldrich) had been intraperitoneally administered one week or more before, and the ascites fluid pooled in the abdominal cavity of each animal was collected.

Both of the two monoclonal antibodies (29-C-8 and 19-E-7) were $IgG_1$.

The obtained monoclonal antibody was purified by using protein A-agarose (Repligen) and reacted with cyanogen bromide-activated Sepharose 4B (mfd. by Pharmacia) to thereby give an immobilized monoclonal antibody gel.

2. STRUCTURAL ANALYSIS OF HIGHLY PURIFIED NATURAL NKAF

Figure 1:
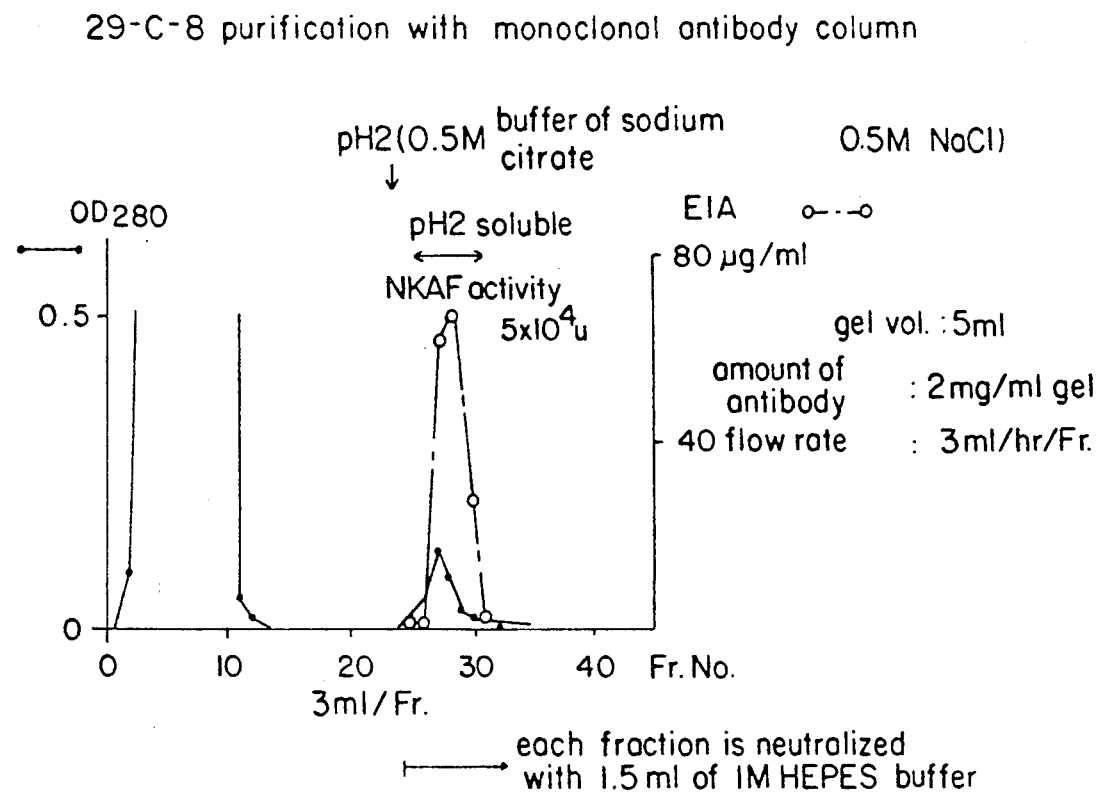
FIG. 1 is a chromatogram which shows the result of the purification of the natural NKAF by a monoclonal antibody column.

The partially purified natural NKAF (Sephadex G-75 fraction) obtained in the above 1-(1) was subjected to affinity chromatography with the use of the immobilized monoclonal antibody gel prepared in the above item (2) and the active fraction was collected (cf. FIG. 1).

The obtained product was a highly purified natural NKAF having a specific activity of approximately $1 \times 10^5$ U/mg of protein.

The properties of this product were analyzed and thus the following results were obtained.

(1) AMINO ACID COMPOSITION ANALYSIS

The desalted natural NKAF was solidified by drying on the bottom of a small test tube for hydrolysis. Then this tube was placed in a glass vial and 500 μl of 6N HCl was poured into the bottom of the vial. Next, the material was evacuated together with the vial, and hydrolyzed with hydrochloric acid at 110° C. for 24 hours. The NKAF hydrolyzate thus obtained was analyzed with an amino acid analyzer 6300 of Beckman System.

Table 1 shows the results.

TABLE 1

| | Amino acid analysis | |
|---|---|---|
| | Found | Calculated |
| Asx | 14.0 | 14 |
| Thr | 11.5 | 13 |
| Ser | 13.2 | 16 |
| Glx | 29.3 | 29 |
| Pro | 8.0 | 9 |
| Gly | 16.4 | 17 |
| Ala | 10.0 | 10 |
| Cys | 9.8 | 12 |
| Val | 11.1 | 12 |
| Met | 2.1 | 2 |
| Ile | 7.6 | 8 |
| Leu | 14.9 | 14 |
| Tyr | 4.7 | 6 |
| Phe | 6.6 | 7 |
| His | 4.2 | 5 |
| Lys | 5.5 | 5 |
| Arg | 21.2 | 19 |

(2) SUGAR COMPOSITION ANALYSIS

The neutral sugar content of the obtained natural NKAF determined by the orcinol-sulfuric acid method was approximately 120 μg/mg of protein. The content of uronic acid therein determined by the carbazole-sulfuric acid method was approximately 300 μg/mg of protein.

Next, the sugar composition of the natural NKAF was analyzed. Table 2 shows the results.

Thus it was confirmed that the obtained natural NKAF was a glycoprotein containing a large amount of O-glycoside type sugar chains (mucopolysaccharides and mucin type sugar chains).

TABLE 2

| | Sugar composition |
|---|---|
| Sugar | Content (μg/mg of protein) |
| N-Acetylglucosamine or N-acetylgalactosamine | 68 μg |
| Mannose | 14 μg |
| Galactose | 55 μg |
| Sialic acid | 54 μg |

(3) DETERMINATION OF NKAF BY EIA

Figure 2:
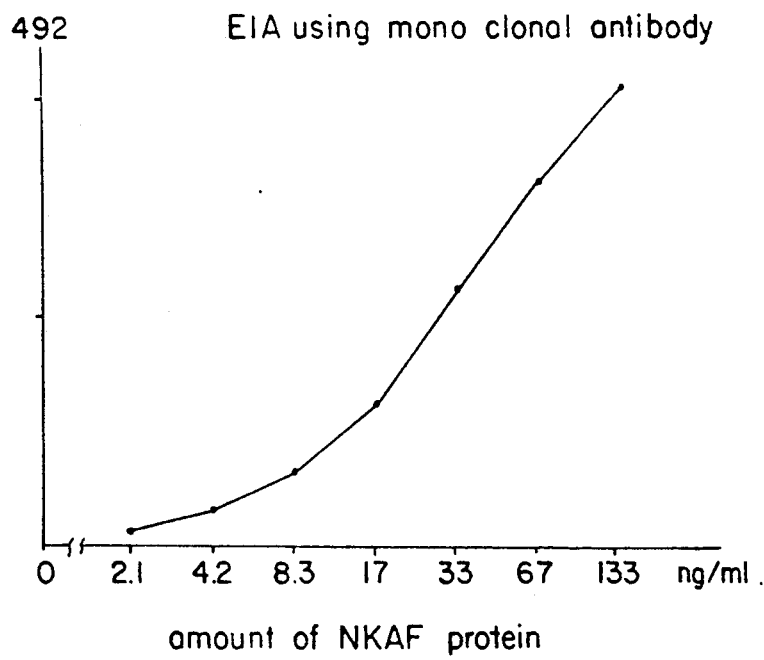
FIG. 2 shows EIA with two monoclonal antibodies.

A well was coated with one of the two monoclonal antibodies, 29-C-8, and washed. Then the NKAF was added thereto and allowed to react at room temperature for one hour. Next, another monoclonal antibody 19-E-7, which had been biotinylated, was added thereto and the mixture was allowed to react at room temperature for one hour. After washing, avidinperoxidase is further added thereto and the obtained mixture was allowed to react at room temperature for 30 minutes. After washing, a solution of o-phenylenediamine, i.e. the substrate, was added. Then color was developed at room temperature. 15 minutes thereafter, the reaction was ceased with 1N HCl and the absorbance ($OD_{492}$) was measured. FIG. 2 shows a calibration curve thus formed.

(4) REMOVAL OF SUGAR CHAINS

Since the NKAF contained a number of sugars, the removal of sugar chains was examined for sequencing amino acids.

The analysis was conducted through SDS-PAGE (sodium dodecyl sulfate-polyacrylamide gel electrophoresis) and Western-immunoblotting. More precisely, the desalted and purified NKAF was treated with sialidase, O-glycanase, chondroitinase and heparitinase and it was examined by the SDS-PAGE whether sugar chains were cleaved thereby or not.

No change was observed before and after the treatment with heparitinase. The molecular weight of the main band of the NKAF was lowered by treating with sialidase or O-glycanase, though the smear did not disappear. When chondroitinase was used, the smear disappeared and a main band was observed at 35 KD. It was confirmed by the Western immunoblotting that this band reacted with the anti-NKAF monoclonal antibody and rabbit anti-NKAF antibody. The activity was sustained after the treatment with chondroitinase.

The desalted and purified NKAF was subjected to reductive carboxamidomethylation and dissolved in 100 mM Tris-HCl buffer (pH 8) containing 0.5 U of chondroitinase and 30 mM $CH_3COONa$. Then it was allowed to react at 37° C. for 60 minutes to thereby cleave the chondroitin sulfate chain.

Figure 3:
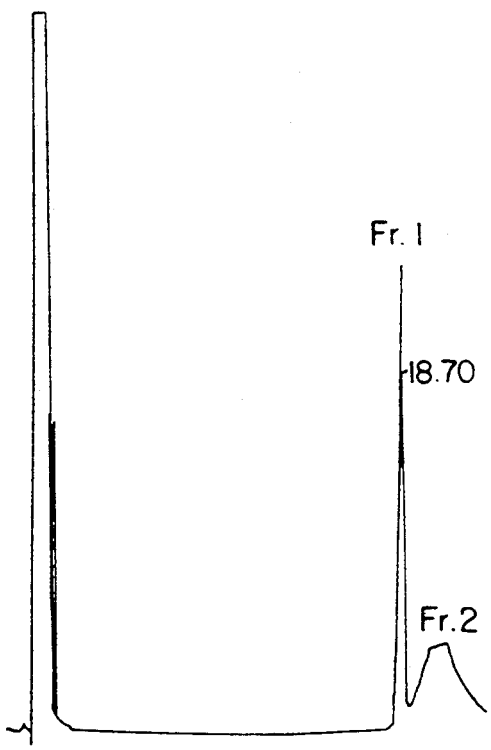
FIG. 3 is a chromatogram which shows the result of the purification of the NKAF by reverse phase HPLC.

The reaction mixture was purified by reverse phase HPLC using a Vydac C4 column and 0.1% TFA (trifluoroacetic acid)/$CH_3CN$ System as a solvent while linearly altering the proportion of the $CH_3CN$ from 0 to 100% within 30 minutes at a flow rate of 1.5 ml/min (cf. FIG. 3).

Figure 4:
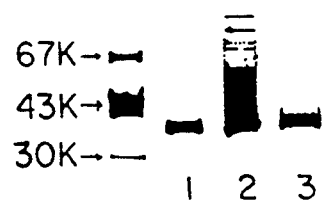
FIG. 4 shows the result of SDS-PAGE.

When Fr.1 and Fr.2 on the chromatogram of FIG. 3 were subjected to the SDS-PAGE, Fr.1 showed a monoband at 35 KD while Fr.2 showed a smear band exceeding 35 KD (cf. FIG. 4). Fr.2 was dissolved in 50 mM Tris-HCl (pH 9) containing 6M of guanidine hydrochloride and subjected to reverse phase HPLC. As a result, Fr.2 migrated toward Fr.1, suggesting that Fr.2 was an aggregation product of Fr.1.

(5) ANALYSIS OF N-TERMINAL AMINO ACID SEQUENCE

The N-terminal amino acid sequence was analyzed by using Fr.1 of FIG. 3. Thus 28 N-terminal residues starting from leucine were specified as follows.
Leu-His-Leu-Arg-Ser-Glu-Thr-XXX-XXX-Phe-Glu-XXX-Pro-Leu-Gly-Ala-Lys-Thr-Leu-Pro-Glu-Asp-Glu-Glu-Thr-Pro-Glu-Gln.

No amino acid appeared on the 8th, 9th and 12th residues. Thus it was assumed as Ser or Thr to which an O-glycoside type sugar chain was bound.

(6) PEPTIDE MAPPING OF NATURAL NKAF ENZYMATICALLY DIGESTED WITH TRYPSIN

Fr.1 of FIG. 3 was dissolved in 0.1M ammonium hydrogen-carbonate (pH 8) containing 2M of urea and trypsin was added thereto. The obtained mixture was allowed to react at 37° C. for 16 hours. After the completion of the reaction, the reaction mixture was purified by reverse phase HPLC using a Vydac C4 column and a solvent system of 0.1% TFA/$CH_3CN$ wherein the proportion of the $CH_3CN$ was linearly altered from 0 to 60% within 1 hour at a flow rate of 1.5 ml/min.

The amino acid composition and amino acid sequences of the 21 peptide fragments thus obtained were analyzed (cf. Table 3).

TABLE 3

| amino acid sequence of peptides digested with trypsin | |
|---|---|
| KR-1 | Ile—Thr—Gly—Ser—Gly—Arg |
| KR-2 | Ala—His—Cys—Leu—Arg |
| KR-3 | Arg—Ala—His—Cys—Leu—Arg |
| KR-5 | Leu—His—Leu—Arg |
| KR-6 | Gly—Gly—His—Cys—Val—Ala—Leu—Cys—Thr—Arg |
| KR-7 | Gly—Gly—Tyr—Trp—Arg |
| KR-8 | Val—Val—Gly—Ile—Pro—Gly—Cys—Gln—Thr—Cys—Arg |
| KR-9 | Leu—His—Leu—Arg—Ser—Glu—Thr—Xxx—Xxx—Phe—Glu—Xxx—Pro—Leu—Gly—Ala—Lys |
| KR-10 | Tyr—Leu—Leu—Val—Arg |
| KR-11 | Phe—Gln—Trp—Val—Asp—Gly—Ser—Arg |
| KR-12 | Arg—Phe—Gln—Trp—Val—Asp—Gly—Ser—Arg |
| KR-13 | Asp—Gly—Ala—Val—Glu—Ser—Ile—Ser—Val—Pro—Asp—Met—Val—Asp—Lys |
| KR-14 | Ile—Gln—Cys—Ser—Val—Ser—Ala—Leu—Asn—Gln—Gly—Gln—Val—Trp—Ile—Gly—Gly—Arg |
| KR-15, 18 | Thr—Leu—Pro—Glu—Asp—Glu—Glu—Thr—Pro—Glu—Gln—Glu—Met—Glu—Glu—Thr—Pro—Cys—Arg |
| KR-16 | Gly—Asn—Leu—Val—Ser—Ile—His—Asn—Phe—Asn—Ile—Asn—Tyr—Arg |
| KR-17 | Arg—Leu—Pro—Phe—Ile—Cys—Ser—Tyr |
| KR-19, 20 | Ser—Leu—Gln—Thr—Phe—Ser—Gln—Ala—Trp—Phe—Thr—Cys—Arg |
| KR-21 | Trp—Asn—Phe—Ala—Tyr—Xxx—Ala—Ala—His—Gln—Pro—Trp—Ser—Arg |

Figure 5:
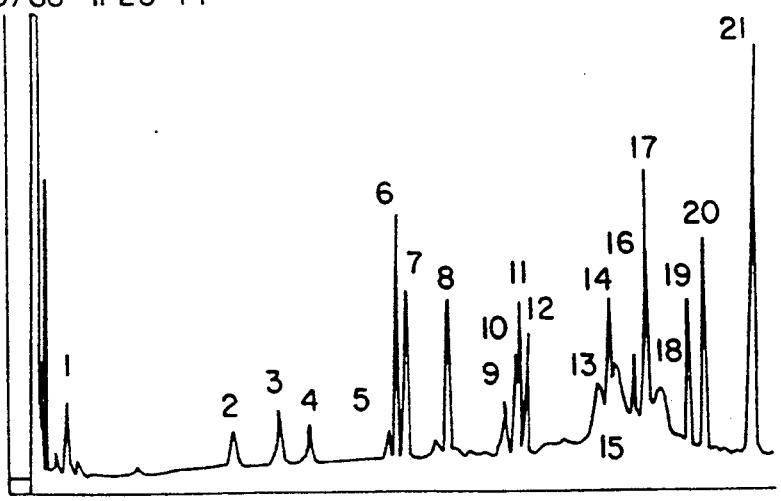

All of the amino acid sequences of the analyzed peptide fragments were identified on the cDNA sequences of the recombinant NKAF which will described hereinbelow (cf. FIGS. 5 and 6).

(7) C-TERMINAL AMINO ACID SEQUENCE

Figure 7:
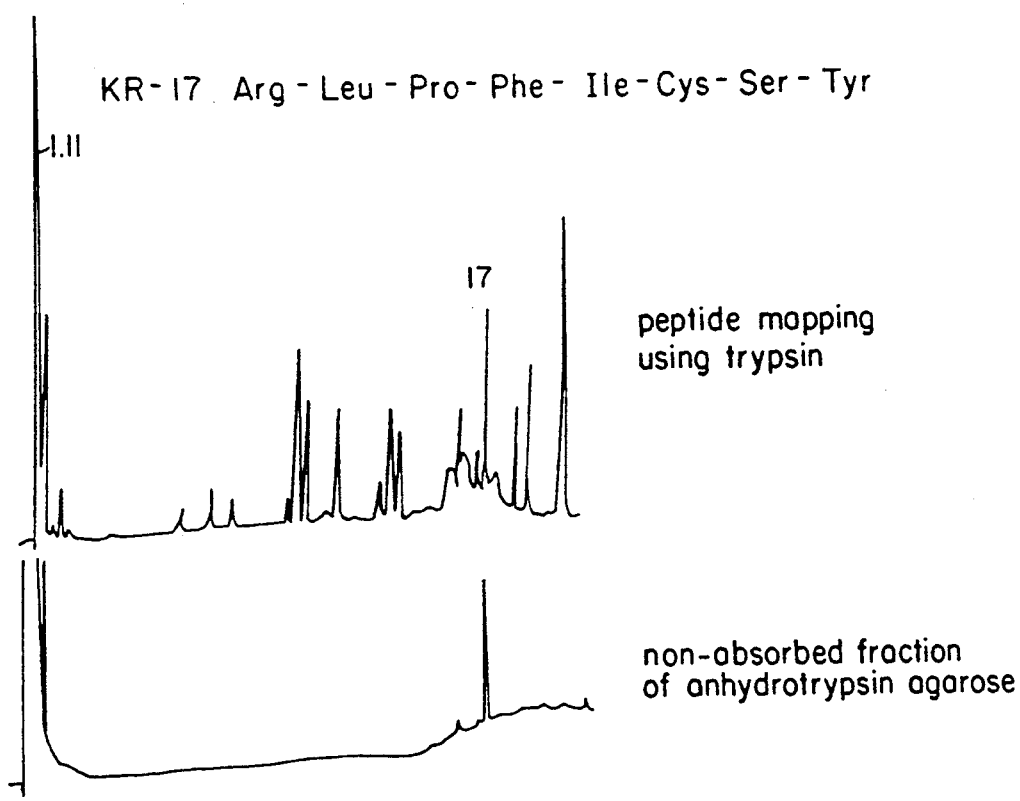
FIG. 7 shows the result of the separation and isolation of the C-terminal peptide.

The tryptic peptides were passed through an anhydrotrypsin agarose column equilibrated with 0.05M sodium carbonate (pH 5) containing 0.02M calcium chloride and unadsorbed fractions were collected. The collected fractions were subjected to reverse phase HPLC under the above conditions to thereby separate the C-terminal peptide fragment (cf. FIG. 7).

As the result of amino acid sequence analysis, the amino acid sequence of this peptide fragment was determined to be Arg-Leu-Pro-Phe-Ile-Cys-Ser-Tyr which agreed with the amino acid sequence of KR-17.

EXAMPLE

Based on the amino acid sequence of the trypsinhydrolyzed fragments of the purified specimen of the natural NKAF, as described above, the base sequence of the mRNA coding for the NKAF is estimated and a DNA oligomer corresponding thereto is synthesized. Next, a cDNA clone having a sequence coding for the NKAF is selected by screening through hybridization of a cDNA library originating from the mRNA of C-108 cells with the use of the above-mentioned oligomer as a probe.

To further illustrate the present invention, the following Examples will be given.

EXAMPLE 1

(1) Isolation of mRNA $1.2 \times 10^9$ cells of KC-8-1-10 C-108 line, which had been stimulated with 4 μl/ml of poke weed mitogen, PWM of GIBCO, in RPMI-1640 medium for eight hours, were collected and RNA was extracted therefrom by a method reported by Chirgwin et al. [Chirgwin, et al., Biochemistry, 18, 5294 (1979)].

3 parts by volume of the extract was then overlaid onto 1 part by volume of a 5.7M CsCl-0.1M EDTA solution and centrifuged at 26000 rpm at 25° for 36 hours with an ultracentrifuging machine (SRP 28 SA Roter; mfd. by Hitachi). Thus the aimed RNA was collected in the form of pellets.

The RNA thus obtained was dissolved in 10 mM Tris-HCl buffer (pH 7.4) and ethanol was added thereto. The obtained mixture was allowed to stand at −70° C. for an hour. The RNA was precipitated by centrifugation and then dissolved in 10 mM Tris-HCl (pH 7.4). KCl was added thereto to a final concentration of 0.5M The obtained mixture was an oligo-(dT)cellulose column [20 mm $\phi \times$ 150 mm] equilibrated with the same buffer. After thorough washing with 0.5M KCl in 10 mM Tris-HCl, the mRNA was eluted with a 10 mM aqueous solution of Tris-HCl.

500 μg of the mRNA originating from the C-108 cells was overlaid on 15 ml of a solution containing a sucrose concentration gradient of 10% to 28% in 50 mM of Tris-HCL having pH of 7.4, 0.2M of NaCl and 1 mM of EDTA. The resulting mixture was centrifuged at 26000 rpm and at 20° C. for 16 hours with an ultracentrifuging machine (SRP 28 Roter; mfd. by Hitachi).

The obtained mixture was fractionated by 500-μl portions and ethanol was added to each fraction to thereby precipitate the mRNA.

The mRNA in each fraction was dissolved in sterilized water in such a manner as to give an mRNA concentration of 1 μg/ml.

Fractions containing mRNA of approximately 2 to 0.5 kb in size were collected and subjected to the subsequent reaction for synthesizing the cDNA.

(2) Formation of cDNA Library

The cDNA was synthesized according to a method reported by U. Gubler et al. [Gubler, U., et al., Gene, 25, 263 (1983)].

Namely, 1 μg of the purified mRNA was treated with an Amersham cDNA synthesizing kit (code No. RPN 12560 of Amersham.

The double-stranded cDNA was passed through a Sepharose CL-6B column and methylated by using a modifying enzyme EcoRI methylase. To the cDNA thus methylated was ligated an EcoRI linker (pGGAATTCC). Next, the material was cleaved with EcoRI to thereby give an EcoRI cohesive end. This cDNA was passed through a Sepharose CL-6B column to thereby remove the excessive EcoRI linker.

The cDNA thus purified was ligated to λgt 11, which had been cut with EcoRI and treated with phosphatase, at a molar ratio of 0.8:1, cDNA:phage DNA and packaged in phage particles. Thus a cDNA library comprising $8 \times 10^6$ to $1.4 \times 10^7$ clones was obtained.

This phage was plated onto ten plates of 15 cm in diameter and grown thereon. Thus 160 ml of a phage solution of a concentration of $10^{11}$ pfu/ml was obtained.

Approximately 90% of the clones in the library had inserts. Eight clones, among ten selected at random, contained inserted cDNA of 300 bp to 2 kbp. The average size of these inserts was 1.2 kbp.

(3) Preparation of DNA Probe

A probe corresponding to the first 12 residues ranging from tryptophan to tryptophan of the amino acid sequence of the trypsin-hydrolyzed fragment KR-21 (W-N-F-A-Y-X-A-A-H-Q-P-W-S-R) of the natural NKAF was prepared.

The unidentified residue X in the above sequence was tentatively assumed to be Ser. If a sugar chain would be bound to this residue, this amino acid should be Ser or Thr. However the analysis of the amino acid composition indicated that this sequence contained no Thr. Thus a probe was prepared based on the assumption that the residue X was Ser.

On the other hand, the sequence of the mRNA coding for KR-21 was estimated by reference to a study on the frequency of the use of human genetic codons [Lathe, R., J. Mol. Biol., 183, 1 (1985)] and a DNA hybridization probe PKR-21 comprising 36 nucleotides complementary therewith was designed.

The sequence of the PKR-21 was as follows:

5'CCATGGCTGGTGGGGCAGCAGAGTAGG-CAAAGTTCCA3'.

It was synthesized by using an automatic DNA synthesizer (mfd. by Applied Biosystems). This probe was 5'-end labelled with $\gamma$-$^{32}$P-ATP and T4 polynucleotide kinase in a conventional manner.

(4) Identification of the cDNA Clones Containing the Coding Sequence of NKAF Approximately 160,000 recombinant phages were screened from the $\lambda$gt 11 cDNA library by the DNA hybridization method with the use of the 32P-labeled PKR-21 probe.

Ten square plates (10×14 cm) were plated with recombinant phages, with approximately 16,000 plaques on each plate. These plaques were transferred onto nitrocellulose membranes in a conventional manner [Mariatis, T. et al., "Molecular Cloning", 320-321 p, Cold Spring Harbor Laboratory (1982)) to thereby denature and immobilize the DNA.

These membranes were pre-hybridized in 6×SSC [1×SSC=150 mM NaCl, 15 mM sodium citrate (pH 7)], 50 mM sodium phosphate (pH 7), 5×Denhardt's (100×Denhardt's=2% bovine serum albumin, 2% polyvinylpyrrolidone, 2% Ficoll) and 100 micrograms per ml calf thymus DNA at 58 degrees C. for two hours.

Next, the membranes were hybridized with the $^{32}$P-labeled PKR-21 probe in 6×SSC, 50 mM sodium phosphate (pH 7) and 5×Denhardt's at 58° C. for approximately 12 hours and washed with 6×SSC-50 mM sodium phosphate at room temperature for 10 minutes twice, at 58° C. for 30 minutes twice and at 65° C. for 45 minutes once. Then clones hybridizing with the pKR-21 were detected by autoradiography.

As a result, approximately 30 plaques were separately hybridized with the PKR-21. cDNAs were cleaved from four clones, among the abovementioned ones, with EcoRI and subcloned in a plasmid vector pBluescript Ⓡ Ks, M13+ (mfd. by Stratagene) to thereby give pNK 8302, pNK 8303, pNK 8306 and pNK 8308 (deposited with Fermentation Research Institute as FERM P-10161, now transferred to the before mentioned international deposit).

Figure 8:
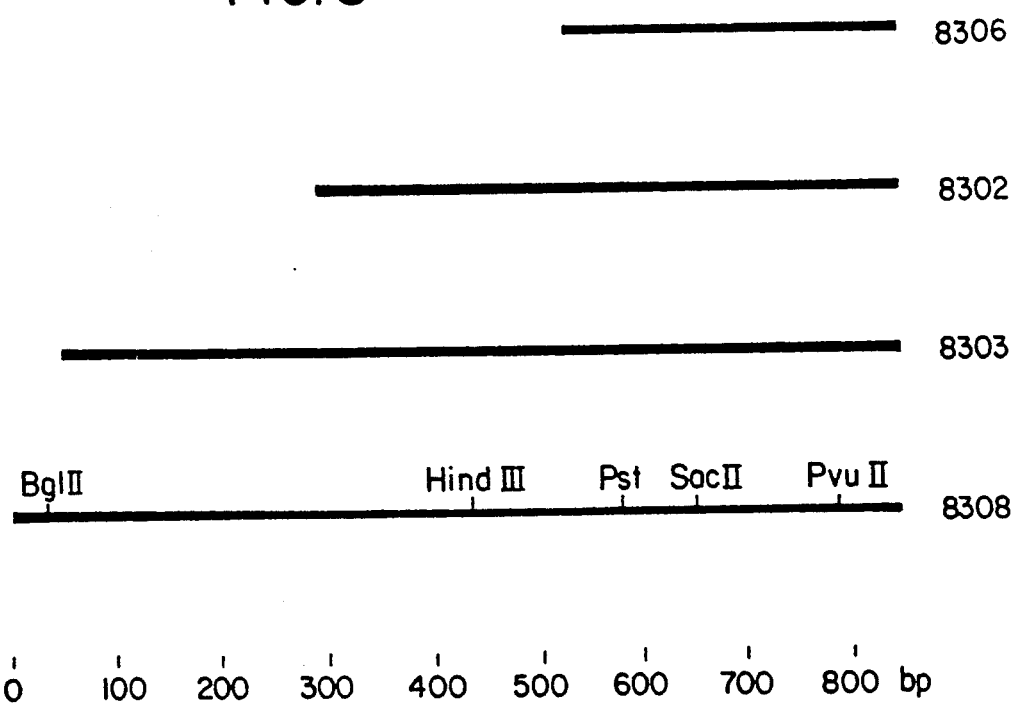
FIG. 8 is the restriction enzyme cleavage map of the cDNA clone.

The base sequences of these cDNA inserts were partially determined by the dideoxy chain termination method [Smith, A., Method in Enzymol., 65, 560; Sanger, F. et al., Proc. Acad. Sci., 74, 5463 (1977)]. As a result, it was found that all of them were cDNAs having various lengths containing sequences coding for the amino acid sequence of the NKAF. FIG. 8 shows the restriction enzyme cleavage maps of them.

Among these cDNAs, the longest one (pNK 8308) had a sequence of 850 bp except poly (A), in which an open reading frame (ORF) (666 bp) starting from an initiator codon and continuously coding 222 amino acid residues was observed (cf. FIG. 9). In this ORF, the peptide sequence of the KR-21 was identified as a fragment ranging from $^{164}$W to $^{177}$R. However the residue X unidentified in the KR-21 was not S but W.

Other trypsin-hydrolyzed peptide sequences were all identified on this ORF, which proved that this cDNA originated from the mRNA coding for the NKAF.

It was known that the N-terminal amino acid sequence of the purified NKAF specimen was $^1$L-$^2$H-$^3$L-$^4$R ..., and it was further suggested that the polypeptide encoded by the cDNA pNK 8308 had a highly hydrophobic additional sequence consisting of 16 residues before the N-terminal sequence.

This might be a signal sequence for secreting the NKAF out of cells which is removed during secretion to thereby give mature NKAF starting from $^1$L.

EXAMPLE 2

Expression of cDNA in COS7 Cells

The pcD vector has the origin of replication and the early promoter of the SV 40 virus. See Okayama, H. and Berg., P., Mol. Cell. Biol., 3, 280 (1983). When the cDNA is integrated downstream of the promoter and introduced into a cell strain COS7, disclosed in Glutzman, Y., Cell., 231, 75(1981), producing the T antigen of the SV40, the recombinant plasmid is amplified which induced transient, high expression of the cDNA.

Figure 10:
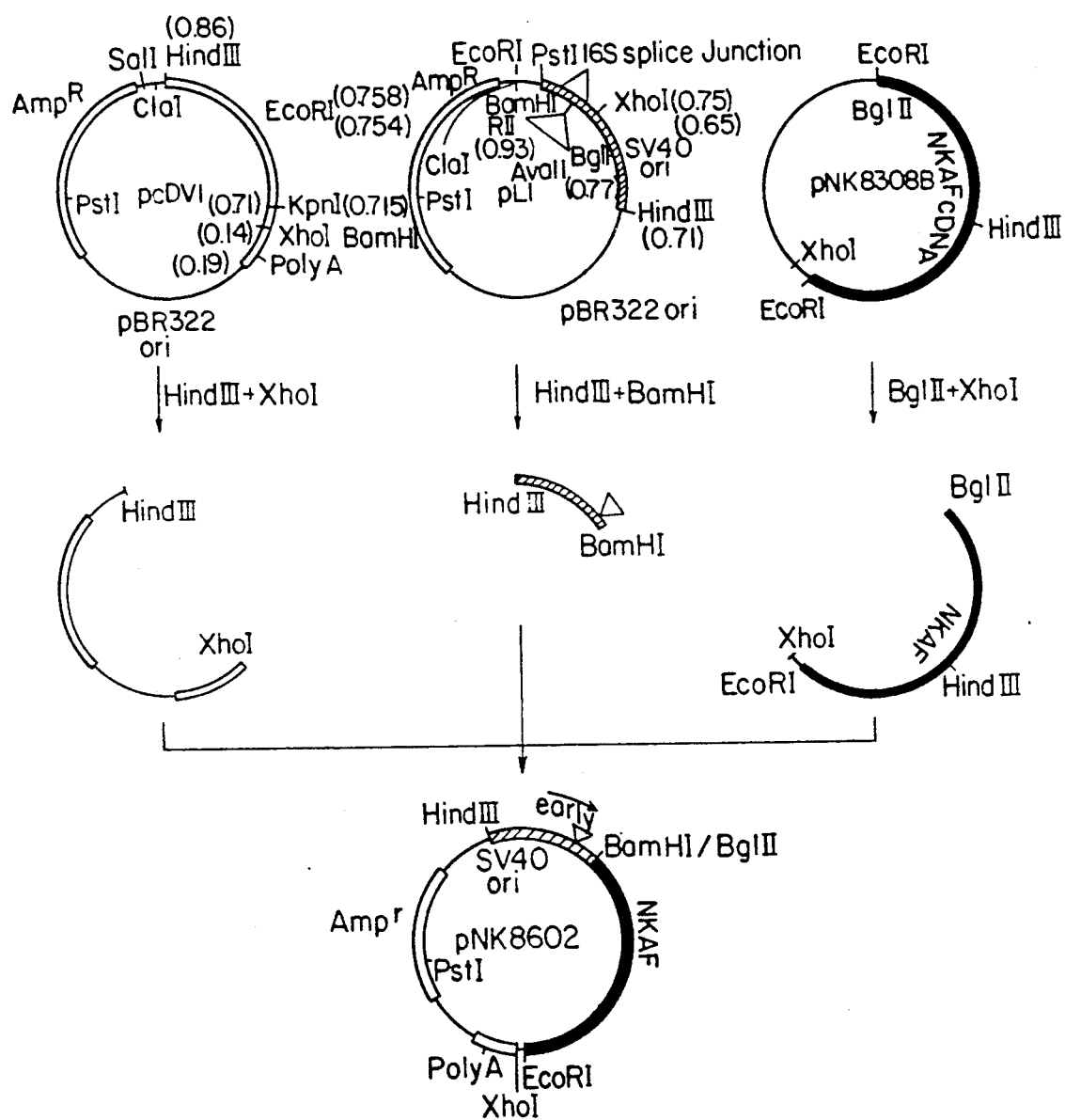
FIG. 10 shows the construction process of pNK 8602 by utilizing pcD vector.

A Bgl II-Xho I fragment involving the whole coding region of NKAF cDNA was excised from the full-length clone pNK 8308 B, and linked to the pcDVl vector cleaved with Xho I and Hind III, together with a Hind III-Bam H I fragment of pLl to thereby form pNK 8602. See FIG. 10. Refer to Okayamam H. and berg, P., Mol. Cell. Biol., 3, 280 (1980).

The cDNA was integrated downstream of the promoter in the correct orientation.

The plasmid DNA of the pNK 8602 was prepared and transfected into COS7 cells by the DEAE-dextran method [Yokohama, T. et al., Proc. Natl. Acad. Sci., 82, 68 (1985)). The cells thus transfected produced NKAF in the culture supernatant approximately one day after transfection and contined the production for approximately five days. See Table 4.

TABLE 4

| | Content ($\mu$g) of pNK 8602 DNA per 9.6 cm$^2$ well | | | | | |
|---|---|---|---|---|---|---|
| | 0 | 0.1 | 0.4 | 1.5 | 6 | 24 |
| 1-2 Day | <0.8 ng/ml | 7.2 ± 0.3 | 13.2 ± 0.3 | 22.2 ± 0.7 | 24.7 ± 0.7 | 33.7 ± 1.3 |
| 2-3 Day | <0.8 | 9.5 ± 0.3 | 16.7 ± 0.2 | 22.7 ± 0.3 | 25.2 ± 0.2 | 30.0 ± 0.2 |
| 3-4 Day | <0.8 | 9.5 ± 0.3 | 16.0 ± 0.7 | 27.3 ± 0.3 | 27.7 ± 0.7 | 32.3 ± 0.8 |
| 4-5 Day | <0.8 | 4.7 ± 0.3 | 10.7 ± 0.7 | 18.2 ± 0.3 | 21.5 ± 1.3 | 25.5 ± 2.0 |

TABLE 4-continued

| | Content (µg) of pNK 8602 DNA per 9.6 cm² well | | | | | |
|---|---|---|---|---|---|---|
| | 0 | 0.1 | 0.4 | 1.5 | 6 | 24 |
| 5-6 Day | <0.8 | 3.8 ± 0.3 | 10.5 ± 0.3 | 14.2 ± 0.7 | 15.5 ± 0.3 | 19.0 ± 0.2 |

Note: Determined by EIA with the use of two monoclonal anitbodies.

In the above determination, either DMEM medium containing 5% of FCS or serum-free HL-1 medium is useful. See Table 5.

TABLE 5

NKAF in culture supernatant of COS7 cells transfected with pNK 8602 (incubated for 6 days)

| Medium | Content of pNK 8602 DNA (µg) | rNKAF (ng/ml) |
|---|---|---|
| HL-1 | 6.25 µg | 48 ± 2 |
| | 25 µg | 55 ± 4 |
| | 100 µg | 54 ± 2 |
| 5% FCS-DME | 25 µg | 46 ± 1 |

Note: Determined by EIA with the use of two monoclonal antibodies.

EXAMPLE 3

Expression of NKAF in Mammalian Cell Lines

MTX(methotrexate)-resistant clones were obtained by co-transfecting the pNK 8602 obtained in Example 1 and pSV2-dhfr (Subramani, S., Mulligan, R., Berg, P., Mol. Cell. Biol., 1, 854 (1981)] to BHK cells (ATCC, CRL 1632 tKts13, Dainippon Seiyaku) either by the elecroporation method (Bio-Rad, Gene Pulser® 0.4 kV/0.4 cm, 500 µF, 10-15 msec, twice) or the calcium phosphate method (Pharmacia, Cell Phect ®) followed by selection with 250 nM of methotrexate.

These clones produced approximately 100 to 1,000 ng/ml of rNKAF in the medium (cf. Table 6).

Furthermore, G418-resistant clones were obtained by co-transfecting the pNK 8602 together with pSV2-dhfr and pSV2-neo [Southern, P. J. & Berg, P., J. Mol. Appl. Gent., 1, 327 (1982)] to CHO-K1 cells by the calcium phosphate method [Kao, F. T. & Puck, T. T., Proc. Natl. Acad. Sci., 60, 1275 (1981)] followed by selection with 1 mg/ml of G-418. The obtained clones were further cultured in medium containing 5 µM of MTX to thereby give clones capable of producing approximately 30 to 400 ng/ml of rNKAF (Cf. Table 7).

TABLE 6

NKAF in BHK/pNK 8602.pSV2-dhfr clone supernatant

| Clone originating from BHK | rNKAF (ng/ml) |
|---|---|
| 1-7 | 1,100 |
| 1-20 | 370 |
| 1-21 | 1,016 |
| 1-105 | 1,048 |
| 2-5 | 576 |
| 2-42 | 798 |
| 2-86 | 173 |

Note: Determined by EIA.

TABLE 7

NKAF in CHO/pNK 8602.pSV2-dhfr.pSV2-neo clone supernatant

| Clone originating from CHO | rNKAF (ng/ml) |
|---|---|
| 3-10 | 37 |
| 3-13 | 37 |
| 3-2a | 423 |
| 3-10a | 313 |
| 3-13a | 375 |

Note: Determined by EIA.

To illustrate the effects of the present invention, the following Test Examples will be given.

TEST EXAMPLE 1

1. Antitumor Activity of Natural NKAF

Plastic-nonadherent PBLs and the NKAF were added to 10% FCS-RPMI-1640 medium and incubated therein at 37° C. for 2.5 hours and 16 hours. Then the cytotoxic activity against $^{51}$Cr-labeled K-562, Molt-4 or Daudi cells was determined to thereby evaluate the NK-activity enhancing effect of the NKAF. Tables 8 and 9 show the results, wherein the control was assumed to be 100%.

TABLE 8

NK-activity enhancing effect of natural NKAF

| | | Exp. 1 | |
|---|---|---|---|
| Target cell | | | K-562 |
| Control | | | 100% |
| Natural NKAF | | 0.5 U/ml | 109 ± 4% |
| | | 1 U/ml | 113 ± 1% |
| | | 2 U/ml | 116 ± 2% |
| | | 4 U/ml | 118 ± 2% |
| | | 8 U/ml | 122 ± 6% |
| r-IL-2 | | 5 U/ml | 122 ± 1% |
| | | Exp. 2 | |
| Target cell | | | K-562 |
| Control | | | 100% |
| Natural NKAF | | 0.6 U/ml | 108 ± 3% |
| | | 1.3 U/ml | 121 ± 1% |
| | | 2.5 U/ml | 126 ± 2% |
| | | 5 U/ml | 129 ± 0% |
| | | 10 U/ml | 134 ± 8% |
| r-IL-2 | | 5 U/ml | 178 ± 14% |

Note: The NK-activity of the control was assued to be 100%.
Exp. 1: NK activity of control: 67%.
Exp. 2: NK activity of control: 40%.

TABLE 9

NK-activity of natural NKAF with various target cells

| | | Target cell | | | | |
|---|---|---|---|---|---|---|
| | | K-562 | | Molt 4 | | Daudi |
| | | Incubation time | | | | |
| | | 2.5 hr | 16 hr | 2.5 hr | 16 hr | 16 hr |
| Control | | 100% | 100% | 100% | 100% | 100% |
| Natural NKAF | 2 U/ml | 138 ± 5% | 124 ± 1% | 247 ± 15% | 159 ± 5% | — |
| | 10 U/ml | 137 ± 7% | — | 245 ± 7% | 171 ± 8% | 190 ± 9% |

TABLE 9-continued

NK-activity of natural NKAF with various target cells

| | | Target cell | | | | |
|---|---|---|---|---|---|---|
| | | K-562 | | Molt 4 | | Daudi |
| | | Incubation time | | | | |
| | | 2.5 hr | 16 hr | 2.5 hr | 16 hr | 16 hr |
| r-IL-2 | 5 U/ml | — | 116 ± 6% | — | 139 ± 8% | 300 ± 4% |
| | 10 U/ml | 129 ± 13% | 132 ± 7% | 198 ± 17% | — | — |
| IFN-γ | 500 U/ml | 109 ± 11% | 144 ± 9% | 170 ± 26% | 141 ± 11% | 251 ± 13% |

As is apparent from Tables 8 and 9, the natural NKAF showed an effect of enhancing the NK activity comparable to those of recombinant interleukin-2 (r-IL-2; mfd. by Shionogi) and interferon-γ (IFN-γ; mfd. by Cellular Products Inc.).

Plastic-nonadherent PBLs were mixed with Raji cells, which had been treated with mitomycin C, and incubated in a 10% FCS-RPMI-1640 medium at 37° C. for six days. Then NKAF was added thereto and the incubation was continued for additional one day. $^{51}$Cr-labeled Raji cells were further added thereto and the incubation was conducted for four hours. Then 100 μl of the supernatant was collected and the $^{51}$Cr radioactivity thereof was measured to thereby examine the activity of killer T cells thus induced by the MLTR (mixed lymphocyte tumor cell reaction). Table 10 shows the results.

Thus it was found that the NKAF enhances the activity of the killer T cells induced by the MLTR.

TABLE 10

| | | Killer T cell activity (%) |
|---|---|---|
| Control | | 42 ± 3 |
| r-IL-2 | 10 U/ml | 59 ± 1 |
| Natural NKAF | 1.6 U/ml | 47 ± 7 |
| | 8 U/ml | 48 ± 1 |
| | 40 U/ml | 56 ± 3 |

TEST EXAMPLE 2

Antitumor activity of the recombinant NKAF

The NKAF activity of the BJK/pNK 8602 pSV$_2$-dhfr clone supernatant was evaluated on the basis of the enhancement of the NK cell activity with the use of human cancer cell strain K-562 cells as target cells. Table 11 shows the results.

The enhancing effect was determined by assuming NK-activity of the control to be 100%. Table 12 shows the results.

Namely, the effects of the recombinant NKAF were almost comparable to those of the natural NKAF.

TABLE 11

NKAF activity of BHK/pNK 8602.pSV$_2$-dhfr clone supernatant

| Clone originating from BHK cell | NKAF activity (U/ml) |
|---|---|
| 1-7 | 160 |
| 1-21 | 80 |
| 2-42 | 40 |
| 1-105 | 120 |

TABLE 12

NK activity of BHK/pNK 8602.pSV$_2$-dhfr clone supernatant (target cell: K-562)

| | | BHK cell clone | |
|---|---|---|---|
| | | 1-7 | 1-21 |
| Dilution of clone supernatant (fold) | 160 | 118 ± 1% | 113 ± 1% |
| | 80 | 123 ± 2% | 113 ± 2% |
| | 40 | 124 ± 5% | 117 ± 1% |
| | 20 | 129 ± 6% | 133 ± 1% |
| Control | | 100% | |
| r-IL-2 | 2.5 U/ml | 125 ± 4% | |

Note: NK activity of control was assumed to be 100%.

EXAMPLE 4

Example Added to NKAF Patent Application (NKAF Expression in *Escherichia coli*)

1. Preparation of Expression Plasmid

The DNA encoding mature NKAF was prepared by removing the signal sequence from NKAF cDNA and was inserted between PL promoter of bacteriopharge λ and to rrnB terminator of *E.coli*. This expression unit was ligated to the vector pBR322 d-rop, which stably maintains a large copy number to construct an expression vector pNK8001.

Figure 11:
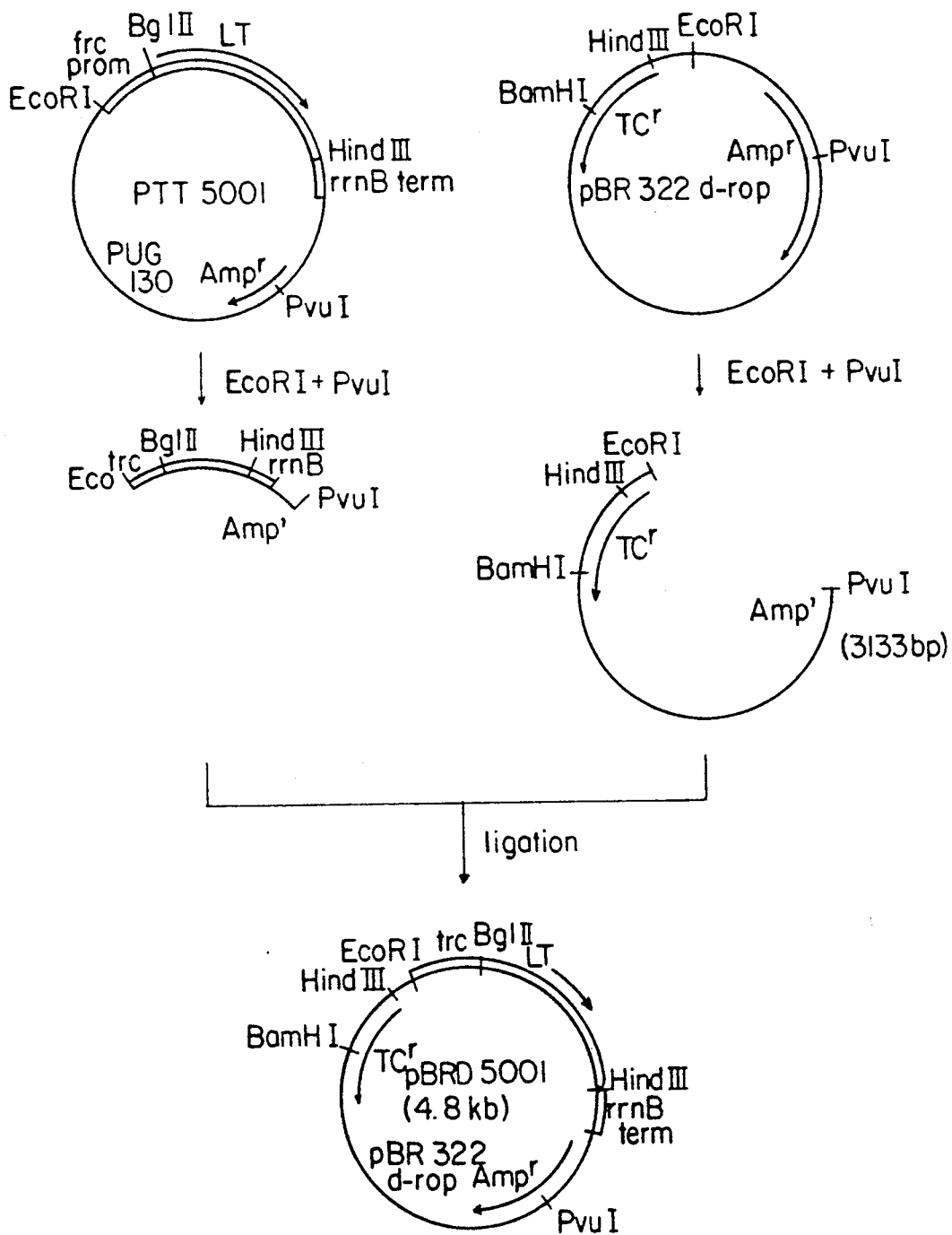
FIG. 11 shows the construction process of the plasmid pBRD 5001, from plasmids ETT 5001 and pBR 322 d-rop.

1) Construction of pBRD5001 (FIG. 11)

pBRD5001 is obtained by replacing the vector portion of the lymphotoxin expression plasmid pTT5001 (Japanese Patent Application 272034/1987 by pBR322 d-rop (Japanese Patent Application 272034/1987 and is expected to stably retain a large copy number of the plasmid. This expression vector has a trc promoter and rrnB terminator derived from pKK233-2 (mfd. by Pharmacia Fine Chemicals Co.).

Figure 12:
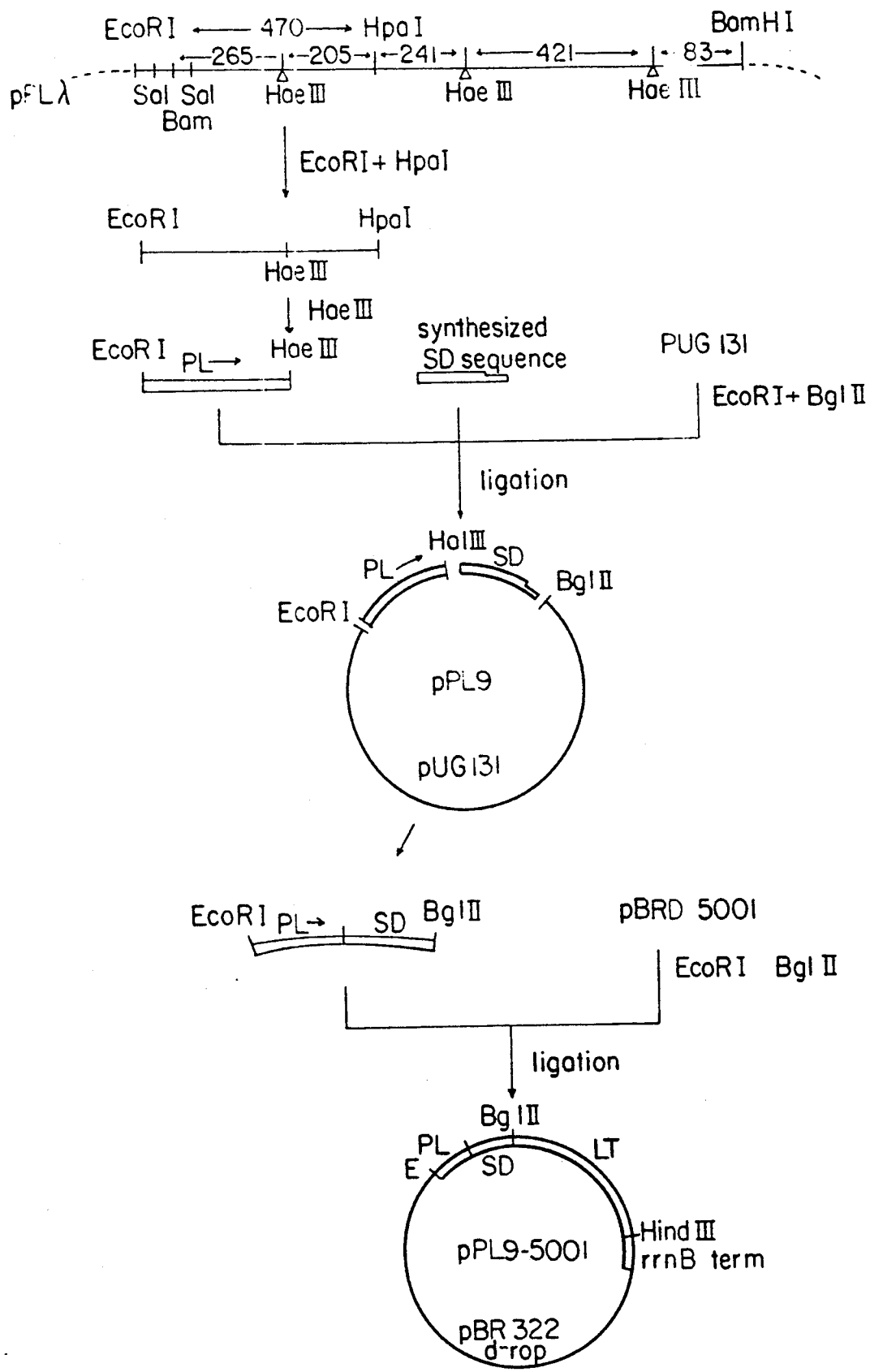
FIG. 12 shows the construction of plasmid pPL9-5001.

2) Construction off pPL9-5001 (FIG. 12)

pPL9-5001 was constructed from pBRD5001, by replacing the promoter with the PL promoter of bacteriopharge λ. pPL- (mfd. by Pharmacia Fine Chemical Co.) was cleaved with EcoRI and HpaI to isolate fragment of approximately 470 bp containing PL promoter. This fragment was cleaved with Hae III to obtain an approximately 265 bp fragment and this fragment was ligated along with the DNA fragment of the following synthetic SD sequence;

5' TTAACAACTAAGGAGGA 3'

3' AATTGTTGATTCCTCCTCTAG 5' to EcoRI-BglII cleaved pUG131 plasmid the plasmid obtained by replacing the polylinker of pUC13 (mfd. by Pharmacia Fine Chemicals Co.) for the polylinker of M13 tg131 (mfd. by Amercham Co.) (Japanese Patent Application 272034/1987)] to generate pPL9.

pBRD5001 was cleaved with EcoRI and Bgl II to remove an approximately 300 bp fragment containing trc promoter and the fragment (PL promoter + SD) of about 280 bp produced by cleaving pPL9 with EcoRI was inserted to create pPL9-5001.

Figure 13:
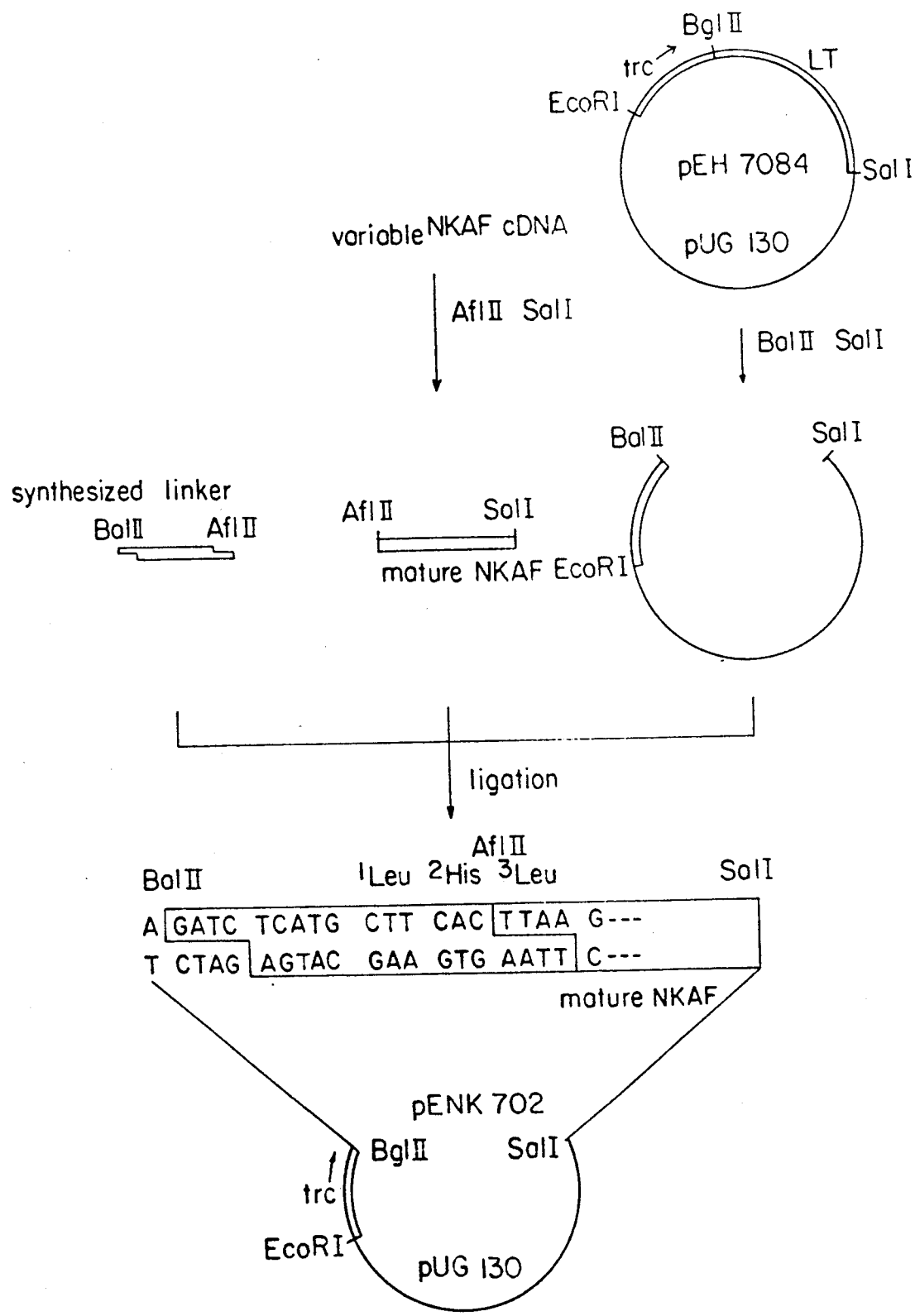
FIG. 13 illustrates the construction of plasmid pENK 702.
Figure 14:
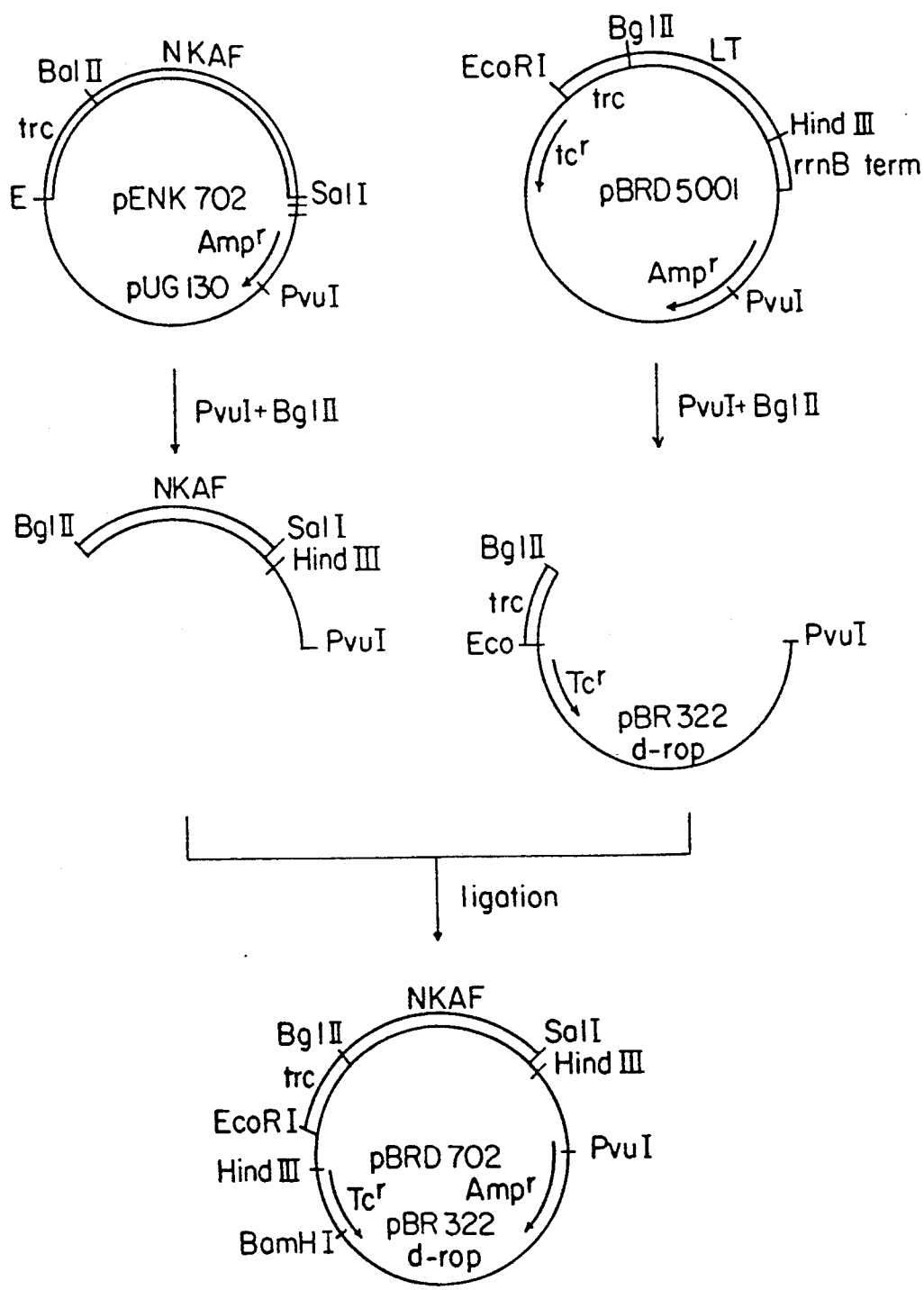
FIG. 14 illustrates the construction of plasmid pBRD 702 from fragments of plasmid pENK 702 and plasmid pBRD 5001.

3) Construction of pBRD702 (FIGS. 13 and 14)

The nucleotide sequence CATATA coding His Leu of NKAF cDNA was converted into CATCTA by in vitro mutagenesis. The mutation introduced a new cleavage site for Afl II.

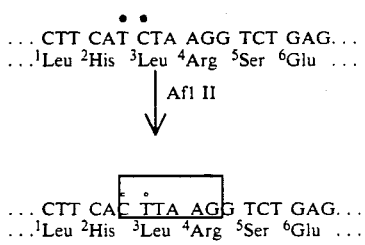

This variant NKAF cDNA was excised with Afl II to create the NKAF fragment without signal sequence. A synthetic DNA linker having a Bgl II-cohesive end and an initiation codon followed by a sequence coding for Leu His was inserted upstream of the NKAF cDNA fragment and ligated to the vector fragment (Bgl II - Sal I) of pEH7084 ( Japanese Patent Application 253302/1988)), creating pENK702 (FIG. 13). In this plasmid, the cDNA coding for the mature NKAF is connected just downstream of the trc promoter of pENK702 via the Bgl II site. A Bgl II - PvuI vector fragment of pBRD5001 and a Bgl II - PvuI NKAF cDNA fragment of pENK702 was then ligated thereto to create pBRD702 (FIG. 14).

Figure 15:
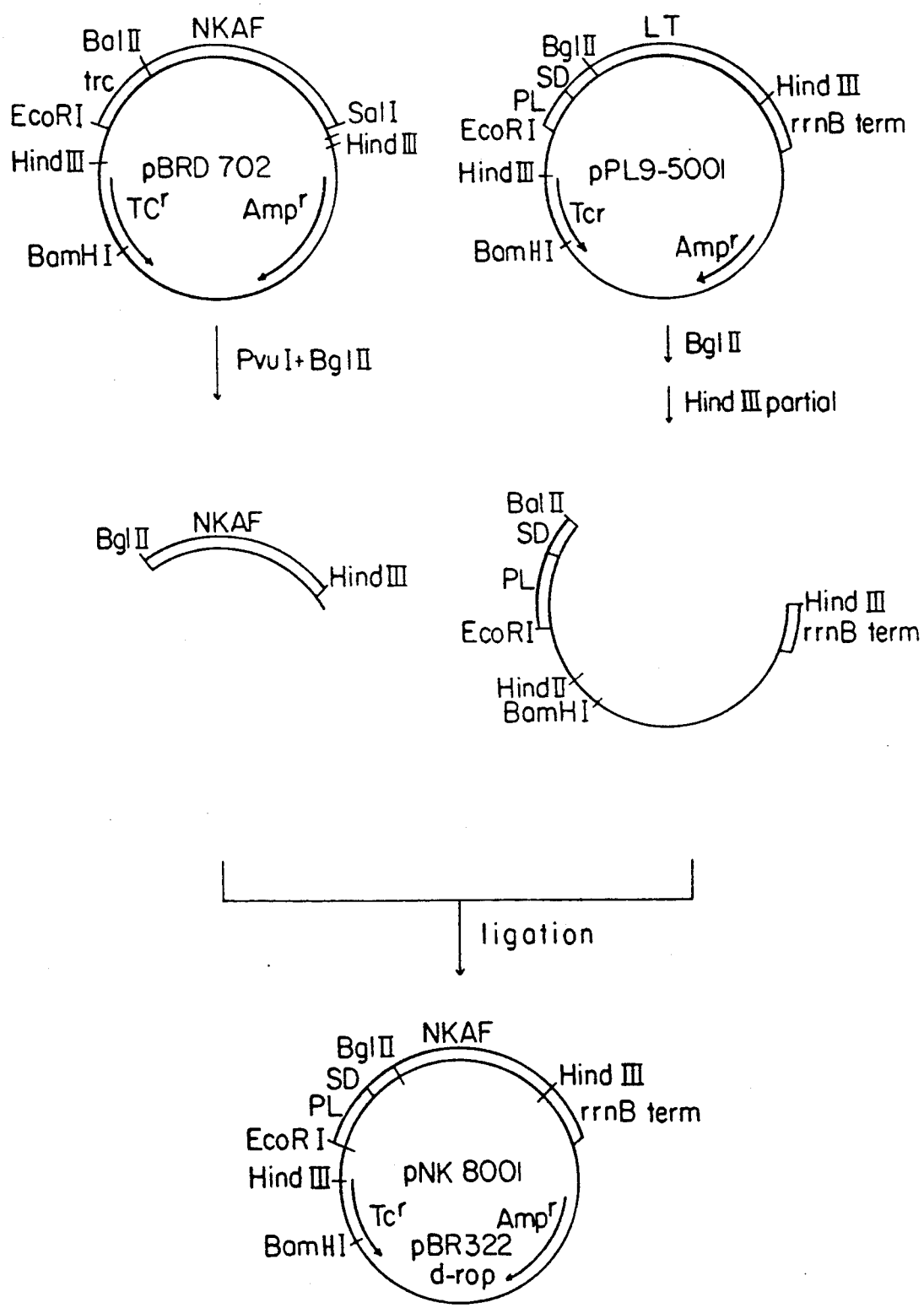
FIG. 15 shows the construction of plasmid pNK 8001 from fragments of plasmids pBRD 702 and pPL9-5005.

4) Construction of pNK8001 (FIG. 15)

pPL9-5001, cleaved with Bgl II and then partially cleaved with Hind III, was separated by agarose-gel electrophoresis to isolate a vector fragment containing a promoter and terminator. On the other hand, pBRD702 was cleaved with Bgl II and Hind III to isolate the NKAF cDNA fragment, which was ligated to the above vector fragment to generate pNK8001. This constructed the expression plasmid having PL promoter, the mature NKAF cDNA and rrnB terminator ligated to pBR322 d-rop vector. The following expression experiments were conducted using pNK8001.

2. NKAF Expression in E.coli

An E. coli strain, N4840 CI857, has a temperature sensitive mutation repressor and induction of the PL promoter is achieved by a high-temperature shift.

pNK8001 and its equivalent lymphotoxin expression plasmid pPL9-5001 were introduced into the strain N4840 via transformation to give an ampicillin-resistant transformants at 30° C. The transformant of each plasmid was grown with shaking in LB medium at 32° C. until OD$_{600}$ of the medium reached about 0.2 (time 0). Then, the temperature was shifted to 42° C. and the culture was continued. After the shift, the culture medium was taken at each designated period and subjected to analysis.

The bacterial cells equivalent to 10 OD$_{600}$ (10 ml of the culture medium in the case of OD-1 were harvested by centrifugation and resuspended in 0.4 ml of the breaking buffer (0.2M Tris of pH 7.6, 0.2M NaCl, 0.01M Mg-Acetate, 0.01M 2-mercaptoethanol, 5% glycerol) Cells were broken by sonication and the homogenate was centrifuged to remove cell debris. Concentration of NKAF in the cell extract was analysed by EIA using rabbit anti-native NKAF antiboty (Table 13). The production of NKAF was observed only in the transformant possessing pNK8001 and its expression was induced by the temperature shift. The production reached maximum at 3 to 5 hours after the shift.

TABLE 13

| Plasmid | NKAF expression in E. coli N 4840 | | | | |
|---------|---|---|---|---|---|
|  | Time after temperature shift | | | | |
|  | 0 | 1.5 | 2 | 5 | 7.5 h |
| pNK8001 | 3 | 5 | 26 | 33 | 19 ng/ml |
| pPL9-5001 | 2 | — | — | — | 3 |

The bacterial extract was subjected to EIA using rabbit anti-native NKAF antibody. One ml of the bacterial extract corresponds to 25 OD$_{600}$ of bacterial cells.

EXAMPLE 5

(1) Preparation of a Expression-Secretion Vector

A DNA encoding mature NKAF was prepared by removing the signal sequence from NKAF cDNA and was inserted downstream the GAL7 promoter alpha-prepro signal sequence. It was connected with YEp13 having a 2 micron replication origin and the expression-secretion vector pYNK1902 was obtained.

(1-1) pTN1071

Figure 16A:
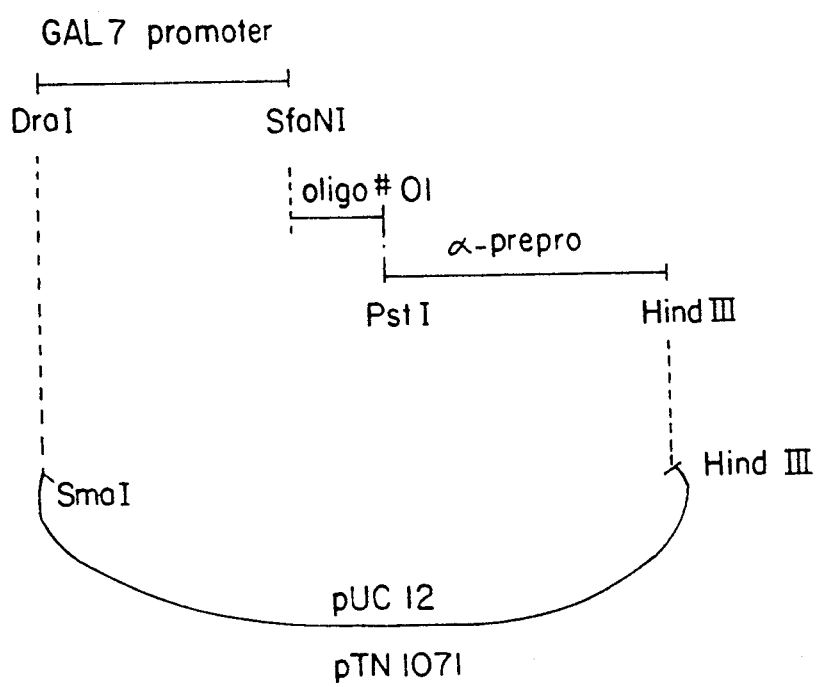
FIG. 16 illustrates the structure of plasmid pTN 1071.

The pTN1071, shown in FIG. 16, has a structure such that the GAL7 promoter disclosed in Japanese patent publication A 60-248181, synthetic OLIGO#01 and alpha-prepro signal sequence disclosed in Herskowitz et al., Cell 30, 933-943, 1982, are inserted into pUC12. The vector has a starting codon ATG at the same position as GAL7 and for this reason it is expected to provide a large amount of protein.

Figure 17:
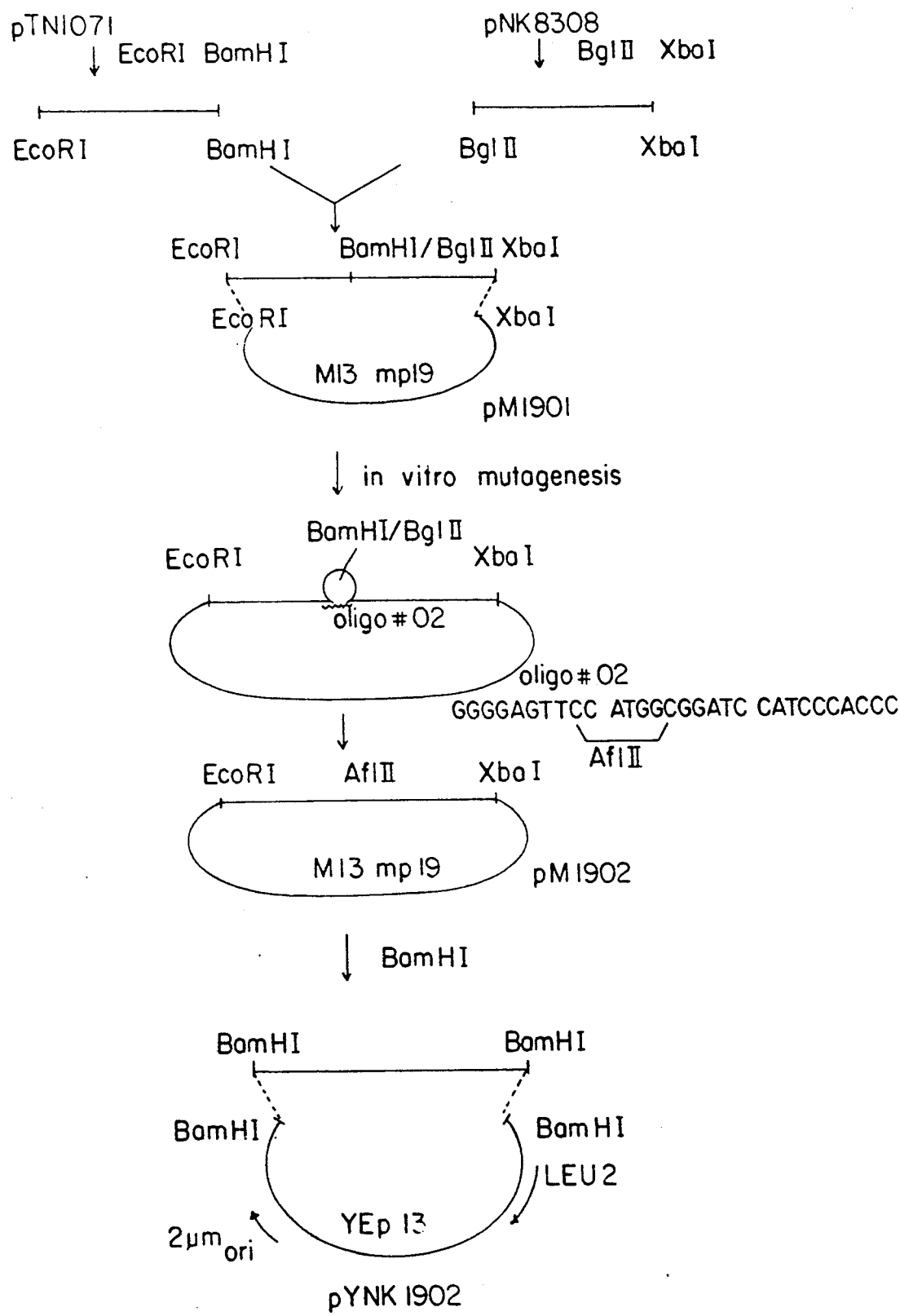
FIG. 17 illustrates the construction of plasmid pYNK1902.

(1-2) pYNK1902 (FIG. 17)

A HindIII-BgIII fragment of pTN1071 and a BgIII-XbaI fragment of pNK8308 were inserted into HindIII, XbaI site of the M13 mp19 disclosed in Messing et al. Gene 33, 103-119, 1985, to obtain pM1901. In vitro mutagenesis was conducted, using the phage for a casting master and synthetic OLTIGO#02, to obtain pM1902 such that the DNA encoding a mature protein of NKAF just after the alpha-prepro signal sequence was added thereto and at the same time an AflII site was inserted thereinto without changing the sequence of amino acids. The pM1902 was cut with BamHI into fragments. The fragment was inserted into YEp13 at the BamHI site to obtain pYNK1902. This plasmid has the GAL7 promoter and so is expected to provide high expression of protein only when a culture does not contain glucose, but uses galactose as a carbon source. Also it is expected to secrete NKAF into the culture because of the alpha-prepro signal sequence.

(2) Expression of NKAF with a Yeast

Using the lithium method disclosed in Ito et al., J. Bacteriol. 153, 163-168, (1983), pYNK1902 was transformed to the yeasts EHA-1C and EHF-2C shown in Table 14. In the data, och2 is a variable species which cannot accept addition of mannose at the non-permissive temperature. See Japanese patent publication A 63-309180. The obtained products were cultivated, being stirred, at 25 degree C. in a selected culture medium containing no leucine. Then glucose was replaced by galactose for the carbon source and the cultivation was continued by elevating the temperature to 34 degree C. Sampling was conducted from time to time. The sample was separated into the cellular and supernatant portions of the culture. The cells were mixed with PBS and glass beads, then disrupted by vortexing and the supernatant of the medium was diluted to conduct EIA to natural NKAF with polyclonal antibody and monoclonal antibody. See Table 15. It was found that NKAF existed in the cells and then it was expressed and secreted into the supernatant of the medium.

TABLE 15

| strain | Genotype |
| --- | --- |
| EHA-1C | a leu2 pep4 gal2 |
| EHF-2C | a leu2 pep4 gal2 och2* |

TABLE 16

| | | EIA (ng/ml/OD600) | | |
| --- | --- | --- | --- | --- |
| | | monoclonal antibody | | polyclonal antibody |
| | hour | cell | broth | cell | broth |
| EHA-1C | 0 | 0 | 0 | 0 | 0 |
| (pYNK1902) | 4 | 5.5 | 0.6 | 9.9 | 1.1 |
| | 10 | 6.5 | 1.3 | 14.5 | 1.6 |
| | 24 | 6.2 | 4.3 | 15.1 | 2.7 |
| EHF-2c | 0 | 0 | 0 | 0 | 0 |
| (pYNK1902) | 4 | 1.7 | 0.9 | 3.1 | 1.4 |

TABLE 16-continued

| | EIA (ng/ml/OD600) | | |
| --- | --- | --- | --- |
| | monoclonal antibody | | polyclonal antibody |
| hour | cell | broth | cell | broth |
| 10 | 3.8 | 3.6 | 7.6 | 6.8 |
| 24 | 3.1 | 6.4 | 5.8 | 13.2 |

We claim:

1. An isolated, purified human natural-killer cell activating factor, comprising a glycoprotein having the amino acid sequence as shown in FIG. 6, of molecular weight approximately 35 kilodaltons, as determined by SDS-PAGE, which increases the killing activity of plastic-nonadherent lymphocytes in a standard cytotoxicity assay using a variety of cell targets.

2. The glycoprotein of claim 1, produced by purification of said natural-killer cell activating factor from a culture of a host cell expressing said factor from a recombinant plasmid.

3. The glycoprotein of claim 2, having as a minimal carbohydrate composition (per mg protein) 68 μg N-Acetylglucosamine or N-Acetylgalactosamine, 14 μg mannose, 55 μg galactose and 54 μg sialic acid.

4. A pharmaceutical composition which comprises a pharmacologically effective amount of the natural-killer cell activating factor, according to claim 1, and a pharmaceutically acceptable carrier.

5. A pharmaceutical composition which comprises a pharmacologically effective amount of the natural-killer cell activating factor, according to claim 2, and a pharmaceutically acceptable carrier.

6. A pharmaceutical composition which comprises a pharmacologically effective amount of the natural-killer cell activating factor, according to claim 3, and a pharmaceutically acceptable carrier.

* * * * *